United States Patent
Jen et al.

(10) Patent No.: US 7,425,643 B1
(45) Date of Patent: Sep. 16, 2008

(54) ELECTRON ACCEPTORS FOR NONLINEAR OPTICAL CHROMOPHORES

(75) Inventors: Kwan-Yue Jen, Kenmore, WA (US); Sei-hum Jang, Mukilteo, WA (US); Jae-Wook Kang, Edmonds, WA (US); Jingdong Luo, Seattle, WA (US); Baoquan Chen, Bothell, WA (US); Sen Liu, Highland Park, NJ (US); Larry R. Dalton, Silverdale, WA (US)

(73) Assignee: University of Washington, Seattle, WA (US)

( * ) Notice: Subject to any disclaimer, the term of this patent is extended or adjusted under 35 U.S.C. 154(b) by 611 days.

(21) Appl. No.: 11/044,986

(22) Filed: Jan. 26, 2005

Related U.S. Application Data

(60) Provisional application No. 60/539,506, filed on Jan. 26, 2004.

(51) Int. Cl.
*C07D 307/30* (2006.01)
*C07D 405/06* (2006.01)

(52) U.S. Cl. ........................................ 549/474; 549/60

(58) Field of Classification Search ................ 549/474, 549/60
See application file for complete search history.

(56) References Cited

U.S. PATENT DOCUMENTS

| | | | |
|---|---|---|---|
| 5,156,774 | A | 10/1992 | Leising et al. |
| 5,432,286 | A | 7/1995 | Cabrera et al. |
| 5,447,662 | A | 9/1995 | Herr et al. |
| 5,489,451 | A | 2/1996 | Omeis et al. |
| 5,514,799 | A | 5/1996 | Varanasi et al. |
| 5,676,884 | A | 10/1997 | Tiers et al. |
| 5,679,763 | A | 10/1997 | Jen et al. |
| 5,693,734 | A | 12/1997 | Herzig et al. |
| 5,718,845 | A | 2/1998 | Drost et al. |
| 5,736,592 | A | 4/1998 | DeMeuse et al. |
| 5,738,806 | A | 4/1998 | Beckmann et al. |
| 5,804,101 | A | 9/1998 | Marder et al. |
| 5,808,100 | A | 9/1998 | Momoda et al. |
| 6,067,186 | A | 5/2000 | Dalton et al. |
| 6,184,540 | B1 | 2/2001 | Chmii et al. |
| 6,211,374 | B1 | 4/2001 | Ippoliti |
| 6,281,366 | B1 | 8/2001 | Frigoli et al. |
| 6,348,992 | B1 | 2/2002 | Zhang et al. |
| 6,361,717 | B1 | 3/2002 | Dalton et al. |
| 6,444,830 | B1 | 9/2002 | He et al. |
| 6,448,416 | B1 | 9/2002 | He et al. |
| 6,584,266 | B1 | 6/2003 | He et al. |
| 6,652,779 | B1 | 11/2003 | Zhang et al. |
| 6,716,995 | B2 | 4/2004 | Huang et al. |
| 6,750,603 | B2 | 6/2004 | Huang et al. |
| 7,084,283 | B2 * | 8/2006 | Ermer et al. ................ 549/474 |
| 2002/0084446 | A1 | 7/2002 | Dalton et al. |

FOREIGN PATENT DOCUMENTS

| | | |
|---|---|---|
| WO | WO 00/009613 A2 | 2/2000 |
| WO | WO 01/53746 A1 | 7/2001 |
| WO | WO 01/56462 A1 | 8/2001 |
| WO | WO 01/77749 A1 | 10/2001 |
| WO | WO 01/79750 A1 | 10/2001 |
| WO | WO 02/08215 A1 | 1/2002 |
| WO | WO 02/14305 A2 | 2/2002 |
| WO | WO 02/29488 A1 | 4/2002 |
| WO | WO 02/37173 A2 | 5/2002 |
| WO | WO 2004/065384 A1 | 8/2004 |
| WO | WO 2004/065615 A2 | 8/2004 |

OTHER PUBLICATIONS

He et al, Chem, Materials, 14, p. 2393-2400 (2002).*
Carrillo, J.R., "The Effect of Focused Microwaves on the Reaction of Ethyl *N*-Trichloroethylidenecarbamate with Pyrazole Derivatives," *Tetrahedron* 55:9623-9630, 1999.
Chen, X., et al., "A Thermally Re-Mendable Cross-Linked Polymeric Material," *Science* 295:1698-1702, Mar. 1, 2002.
Dalton, L., "Polymeric Electro-Optic Materials: Optimization of Electro-Optic Activity, Minimization of Oprtical Loss, and Fine-Tuning of Device Performance," *Opt. Eng.* 39(3):589-595, Mar. 2000.
Dalton, L.R., et al., "From Molecules to Opto-Chips: Organic Electro-Optic Materials," *J. Mater. Chem.* 9:1905-1920, 1999.
Goussé, C., et al., "Application of the Diels-Alder Reaction to Polymers Bearing Furan Moieties. 2. Diels-Alder and Retro-Diels-Alder Reactions Involving Furan Rings in Some Stryrene Copolymers," *Macromolecules* 31:314-421, 1998.
He, M., et al., "Synthesis of Chromophores with Extremely High Electro-Optic Activity. 1. Thiophene-Bridge-Based Chromophores," *Chem. Mater.* 14:4662-4668, 2002.
Kwart, H., and K. King, "The Reverse Diels-Alder or Retrodiene Reaction," *Chem. Rev.* 68(4):415-447, Aug. 1968.
Liu, S., et al., "Focused Microwave-Assisted Synthesis of 2,5-Dihydrofuran Derivatives as Electron Acceptors for Highly Efficient Nonlinear Optical Chromophores," *Adv. Mater.* 15(7-8):603-607, 2003, retrieved from Caplas as 2003: 338986.
Luo, J., et al., "Design, Synthesis, and Properties of Highly Efficient Side-Chain Dendronized Nonlinear Optical Polymers for Electro-Optics," *Adv. Mater.* 14(23):1763-1768, Dec. 3, 2002.

(Continued)

*Primary Examiner*—Bernard Dentz
(74) *Attorney, Agent, or Firm*—Christensen O'Connor Johnson Kindness PLLC

(57) ABSTRACT

Electron acceptor compounds, nonlinear optical chromophores made from the electron acceptor compounds, methods for making the electron acceptor compounds and nonlinear optical chromophores, lattices that include the nonlinear optical chromophores, and devices that include the nonlinear optical chromophores.

3 Claims, 14 Drawing Sheets

OTHER PUBLICATIONS

Luo, J., et al., "Recent Progress in Developing Highly Efficient Nonlinear Optical Chromophores and Side-Chain Dendronized Polymers for Electro-Optics," *Proceeding of SPIE*, The International Society for Optical Engineering, San Jose, California, Jan. 25-31, 2003, vol. 4491 (53): pp. 520-529, retrieved from Caplus as 2003:632269.

Ma, H., et al., "Polymer-Based Optical Waveguides: Materials, Processing, and Devices," *Adv. Mater.* 14(19):1339-1365, Oct. 2, 2002.

McElhanon, J.R., and D.R. Wheeler, "Thermally Responsive Dendrons and Dendrimers Based on Reversible Furan-Maleimide Diels-Alder Adducts," *Org. Lett.* 3(17):2681-2683, 2001.

Melikian, G., et al., "Synthesis of Substituted Dicyanomethylendihydrofurans," *Synth. Commun.* 25(19):3045-3051, 1995.

Villemin, D., and L. Liao, "Rapid and Efficient Synthesis of 2-[3-Cyano-4-(2-Aryliden)-5, 5-Dimethyl-5H-Furan-2-Ylidene]-Malononitrile Under Focused Microwave Irradiation," *Synth. Commun.* 31(11):1771-1780, 2001.

Yoon, S.S., and W.C. Still, "Sequence-Selective Peptide Binding With a Synthetic Reception," *Tetrahedron* 51(2):567-578, 1995.

Zhang, C., et al., "A Novel Trilinkable High μβ NLO Chromophore for Polymeric Electro-Optic Material With Enhanced Thermal Stability," *Am. Chem. Soc., Div. of Polymer Chem.* 40(1):156-157, 1999, retrieved from Caplus as 1999: 211124.

* cited by examiner

ELECTRON ACCEPTORS FOR NONLINEAR OPTICAL CHROMOPHORES

CROSS-REFERENCE TO RELATED APPLICATION

This application claims the benefit of U.S. Provisional Patent Application No. 60/539,506, filed Jan. 26, 2004.

STATEMENT OF GOVERNMENT LICENSE RIGHTS

The U.S. Government has a paid-up license in this invention and the right in limited circumstances to require the patent owner to license others on reasonable terms as provided for by the terms of Contract No. DMR-120967, awarded by the National Science Foundation, and Contract No. N000140410094, awarded by the Defense Advanced Research Projects Agency.

FIELD OF THE INVENTION

The present invention relates to electron acceptors and nonlinear optical chromophores that include the acceptors that are useful in electro-optic devices.

BACKGROUND OF THE INVENTION

Electrical signals can be encoded onto fiber-optic transmissions by electrooptic modulators. These modulators include electro-optic materials having highly polarizable electrons. When these materials are subject to an electric field, their polarization changes dramatically resulting in an increase in the index of refraction of the material and an accompanying decrease in the velocity of light travelling through the material. This electric field-dependent index of refraction can be used to encode electric signals onto optical signals. Uses include, for example, switching optical signals and steering light beams.

A variety of electro-optic materials have been utilized for use in electro-optic devices. Among these materials are inorganic materials such as lithium niobate, semiconductor materials such as gallium arsenide, organic crystalline materials, and electrically-poled polymer films that include organic chromophores. A review of nonlinear optical materials is provided in L. Dalton, "Nonlinear Optical Materials", Kirk-Othmer Encyclopedia of Chemical Technology, 4th Edition, Volume 17 (John Wiley & Sons, New York, 1995), pp. 288.

In contrast to inorganic materials in which polar optical lattice vibrations diminish their effectiveness, the optical properties of organic nonlinear optical materials depend primarily on the hyperpolarizability of their electrons without a significant adverse contribution from the lattice polarizability. Thus, organic nonlinear optical materials offer advantages for ultrafast electro-optic modulation and switching.

Lithium niobate, a common material currently utilized in electro-optic devices, has an electro-optic coefficient of about 35 pm/V resulting in a typical drive voltage of about 5 volts. Drive voltage ($V\pi$) refers to the voltage required to produce a $\pi$ phase shift of light. Lithium niobate has a high dielectric constant ($\in=28$), which results in a mismatch of electrical and optical waves propagating in the material. The mismatch necessitates a short interaction length, which makes drive voltage reduction through increasing device length unfeasible, thereby limiting the device's bandwidth. Recent lithium niobate modulators have been demonstrated to operate at a bandwidth of over 70 GHz.

Electro-optic poled polymers have also been utilized as modulating materials. Their advantages include their applicability to thin-film waveguiding structures, which are relatively easily fabricated and compatible with existing microelectronic processing. These polymers incorporate organic nonlinear optically active molecules to effect modulation. Because organic materials have low dielectric constants and satisfy the condition that $n^2=\in$, where n is the index of refraction and $\in$ is the dielectric constant, organic electro-optic will have wide bandwidths. The dielectric constant of these materials ($\in=2.55-4$) relatively closely matches the propagating electrical and optical waves, which provides for a drive voltage in the range of about 1-2 volts and a bandwidth greater than 100 GHz.

Advantages of organic nonlinear optical materials include a bandwidth in excess of 100 GHz/cm device and ease of integration with semiconductor devices. See, L. Dalton et al., "Synthesis and Processing of Improved Organic Second-Order Nonlinear Optical Materials for Applications in Photonics", Chemistry of Materials, Vol. 7, No. 6, pp. 1060-1081 (1995). In contrast to inorganic materials, these organic materials can be systematically modified to improve electro-optic activity by the design and development of new organic materials and by the development of improved processing methods. See, L. Dalton et al., "The Role of London Forces in Defining Noncentrosymmetric Order of High Dipole Moment-High Hyperpolarizability Chromophores in Electrically Poled Polymeric Films", Proceedings of the National Academy of Sciences USA, Vol. 94, pp. 4842-4847 (1997).

For an organic nonlinear optical material to be suitable for electro-optic applications, the material should have a large molecular optical nonlinearity, referred to as hyperpolarizability ($\beta$), and a large dipole moment ($\mu$). A common figure of merit used to compare materials is the value $\mu\beta$. See Dalton et al. (1997). Organic materials having $\mu\beta$ values greater than about $15,000 \times 10\text{-}48$ esu that also satisfy the requirements of thermal and chemical stability and low optical loss at operating wavelengths have only recently been prepared. See Dalton et al., "New Class of High Hyperpolarizability Organic Chromophores and Process for Synthesizing the Same", WO 00/09613. However, materials characterized as having such large $\mu\beta$ values suffer from large intermolecular electrostatic interactions that lead to intermolecular aggregation resulting in light scattering and unacceptably high values of optical loss. See Dalton et al. (1997).

Thus, the effectiveness of organic nonlinear optical materials having high hyperpolarizability and large dipole moments is limited by the tendency of these materials to aggregate when processed into electro-optic devices. The result is a loss of optical nonlinearity. The stability of these materials also limits their utility. Accordingly, there exist a need for improved nonlinear optically active materials having large hyperpolarizabilities, large dipole moments, and high stability and that, when employed in electro-optic devices, are stable and exhibit large electrooptic coefficients. The present invention seeks to fulfill these needs and provides further related advantages.

SUMMARY OF THE INVENTION

In one aspect, the invention provides electron acceptor compounds. The electron acceptor compounds have utility in organic nonlinear optical applications. Methods for making the electron acceptor compounds are also provided.

In another aspect, the invention provides nonlinear optical chromophores made from the electron acceptor compounds of the invention. Methods for making the nonlinear optical chromophores are also provided.

In other aspects, the invention provides lattices that include the nonlinear optical chromophores and devices that include the nonlinear optical chromophores are provided.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Figure 1:
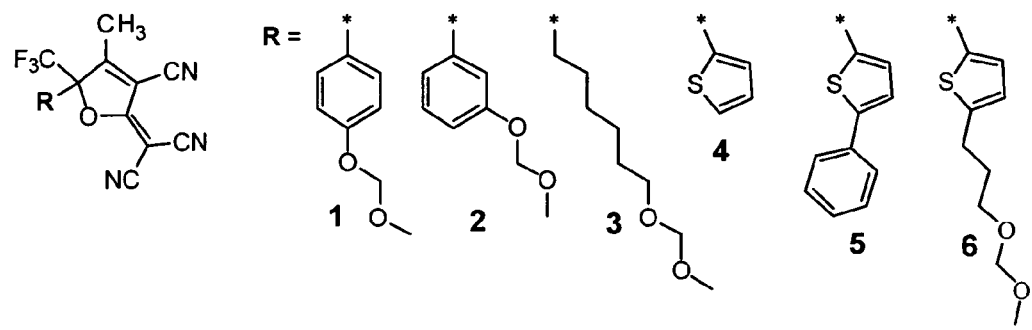
FIG. 1 is an illustration of several representative electron acceptor compounds of the invention.

In one aspect, the invention provides electron acceptor compounds. The electron acceptor compounds have utility in organic nonlinear optical (NLO) applications. The electron acceptor compounds exhibit high thermal and chemical stability.

The electron acceptor compounds can be used to make stable, nonlinear optical chromophores having large hyperpolarizabilities, large dipole moments, and that, when employed in electro-optic devices, exhibit large electrooptic coefficients. NLO chromophores made from the electron acceptor compounds of the invention include an electron acceptor group (i.e., the portion of the chromophore derived from the electron acceptor compound). The electron acceptor group serves as an electron acceptor and further imparts advantageous properties to the chromophore. The chromophores of the invention are described below.

As used herein, the term "electron acceptor group" or "electron withdrawing group" refers to an electronegative organic substituent in a compound having a π-electron system that includes the electronegative organic substituent, where the electronegative organic substituent attracts electron density from the π-electron system when the compound is polarized by electromagnetic energy.

The term "electron acceptor compound" refers to a compound that is useful in making a nonlinear optical chromophore having an electron acceptor group, where the electron acceptor group is derived from the electron acceptor compound.

The electron acceptor compounds of the invention include one or more substituents that impart improved properties to the compounds and the NLO chromophores that include electron acceptor groups derived from the compounds. The improved properties relate to enhanced acceptor compound and chromophore stability, reduced close packing resulting in enhanced chromophore poling efficiency, and the capability of further chemical manipulation to further derivatize or functionalize the compound and chromophore.

Electron Rich Substituent. The electron acceptor compounds of the invention include one or more electron rich substituents. As used herein, the term "electron rich substituent" refers to a substituent having electron donating character. Through its electron donating character, the electron rich substituent stabilizes neighboring electropositive atoms (i.e., electrophilic atoms). Electron donating character is opposite electron withdrawing character. The electron rich substituent serves to stabilize the acceptor compound. Although the electron acceptor compounds of the invention include one or more electron rich substituents, the compounds themselves remain electronegative overall. The presence of one or more electron rich substituents renders the acceptor compound chemically stable (e.g., less reactive toward nucleophilic attack) and thereby allows for a wide variety of chemical manipulations that are either not possible or difficult to achieve with electron acceptor compounds that do not include one or more electron rich substituents. NLO chromophores that include electron acceptor groups having one or more electron rich substituents (i.e., a chromophore made from an acceptor compound of the invention) have enhanced stability compared to similarly constituted chromophores that lack the electron rich substituent. In one embodiment, the NLO chromophores of the invention have an electron acceptor group having one or more electron rich substituents.

Representative electron rich substituents include phenyl ether substituents and thiophenyl substituents. Suitable phenyl ether substituents include 4-methoxymethyl phenyl ether and 3-methyoxymethyl phenyl ether substituents (see FIG. 1, Compounds 1 and 2, respectively). Suitable thiophenyl substituents include 2-thiophenyl, 5-phenyl-2-thiophenyl, and 5-(3-methoxymethyl propyl ether)-2-thiophenyl substituents (see FIG. 1, Compounds 4, 5, and 6, respectively).

Chromophore Agregation. Intermolecular attractive forces can cause chromophore aggregation diminishing hyperpolarizability and electro-optic coefficient. Chromophore design can reduce/eliminate aggregation increasing chromophore hyperpolarizability and electro-optic coefficient.

Many molecules can be prepared having high hyperpolarizability values, however their utility in electro-optic devices is often diminished by the inability to incorporate these molecules into a host material with sufficient noncentrosymmetric molecular alignment to provide a device with acceptable electro-optic activity. Molecules with high hyperpolarizability typically exhibit strong dipole-dipole interactions in solution or other host material that makes it difficult, if not impossible to achieve a high degree of noncentrosymmetric order unless undesirable spatially anisotropic intermolecular electrostatic interactions are minimized.

Chromophore performance is dependent on chromophore shape. See Dalton et al., "Low (Sub-1-Volt) Halfwave Voltage Polymeric Electro-optic Modulators Achieved by Controlling Chromophore Shape", *Science*, Vol. 288, pp. 119-122 (2000). In certain embodiments, the chromophores of the invention have shapes that reduce the disadvantageous intermolecular interactions. The chromophores include substituents that sterically inhibit such interactions. Traditionally, these chromophores includes one or more substituents on donor group or bridge portion of the chromophore.

In one embodiment, the electron acceptor compounds of the invention include one or more substituents that inhibit aggregation. NLO chromophores made from the electron acceptor compounds of the invention that include one or more substituents that inhibit aggregation have reduced close packing, reduced disadvantageous intermolecular interactions, and increased site isolation, resulting in improved poling efficiency.

In one embodiment, the NLO chromophores of the invention have an electron acceptor group having one or more substituents that inhibit aggregation. The chromophores of the invention can include combinations of donors and/or bridges, also having one or more of which can include substituents to provide site isolation. Thus, in certain embodiments, the invention provides chromophores that have electron acceptor groups having one or more substituents effective to reduce intermolecular chromophore association. In certain embodiments, the invention provides spherical, and nearly spherical, chromophores.

Representative electron acceptor compound substituents that enhance site isolation and chromophore poling include aryl groups, such as substituted and unsubstituted aryl groups, for example, phenyl, naphthyl, thiophenyl groups.

In one embodiment, the substituent that enhances chromophore poling is a substituted or unsubstituted phenyl, for example, a phenyl ether substituent. In one embodiment, the substituent that enhances chromophore poling is a substituted or unsubstituted thiophenyl substituent.

Chemical Modification. The electron acceptor compounds of the invention include one or more substituents having chemical reactivity sufficient to readily further derivatize or functionalize the compound. In this aspect, the substituent can include a protecting group that can be readily removed to provide a functional group that can be further reacted to provide a modified acceptor compound.

In one embodiment, the chromophores of the invention have an electron acceptor group that includes one or more substituents having chemical reactivity sufficient to readily further derivatize or functionalize the chromophore.

Representative functional groups include any functional group that can be readily protected, deprotected, and then further reacted. Exemplary functional groups include hydroxy, amino, thiol, phenol, and carboxy groups. Suitable protecting groups for hydroxy, amino, thiol, phenol, and carboxy groups are well known and can be used in the practice of the invention. For a description of protecting groups useful in the practice of the invention, see Protective Groups in Organic Synthesis, Theodora W. Greene, John Wiley & Sons, Inc., New York, N.Y., 1981.

The functional group can be further reacted with a suitable reagent or compound to provide a modified compound having desired properties. For example, the functional group can be reacted with a suitably functionalized dendron to provide a dendronized electron acceptor compound or dendronized chromophore. The functional group can be reacted with a suitably functionalized compound having a crosslinkable group to provide a crosslinkable electron acceptor compound or crosslinkable chromophore.

In one embodiment, the substituent having chemical reactivity sufficient to readily further derivatize or functionalize the compound is a phenyl ether, for example, a methoxymethyl phenyl ether (i.e., $CH_3OCH_2OC_6H_5$—), which can be readily deprotected to provide a phenol (i.e., $HOC_6H_5$—) that can be further functionalized.

Other suitable phenol protecting groups useful in the invention include ethers, such as methyl, methoxymethyl, 2-methoxyethoxymethyl, methylthiomethyl, tetrahydropyranyl, phenacyl, cyclopropylmethyl, allyl, isopropyl, cyclohexyl, t-butyl, benzyl, o-nitrobenzyl, 9-anthrylmethyl, and 4-picolyl ethers; silyl ethers, such as trimethylsilyl and t-butyldimethylsilyl ethers; esters, such as acetates, pivolates, benzoates, 9-fluorenecarboxylates; and carbonates, such as methyl, 2,2,2-trichloroethyl, vinyl, and benzyl carbonates.

In one embodiment, the electron rich substituent enhances site isolation and chromophore poling, and also has reactivity suitable for further chemical modification.

In one embodiment, the electron acceptor compounds of the invention have the formula (I):

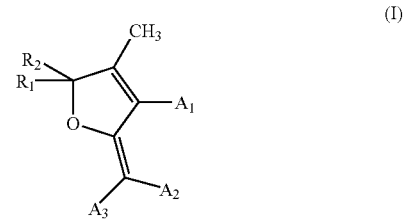

For the above compounds, at least one of $R_1$ or $R_2$ is an electron rich substituent and $A_1$, $A_2$, and $A_3$ are electron withdrawing groups.

Suitable electron rich substituents ($R_1$) include phenyl ethers, thiophenes, phenyl substituted thiophenes, and alkyl ether substituted thiophenes. FIG. 1 illustrates several representative electron acceptor compounds of the invention having electron rich substituents (see FIG. 1, Compounds 1, 2, 4, 5, and 6).

When $R_2$ is not an electron rich substituent, $R_2$ is selected from alkyl, aryl, and heteroalkyl substituents as defined below.

The term "alkyl" refers to a saturated or unsaturated, straight or branched, cyclic or multicyclic aliphatic (i.e., non-aromatic) hydrocarbon group containing from 1 to about 30 carbons. Independently the hydrocarbon group, in various embodiments: has zero branches (i.e., is a straight chain), one branch, two branches, or more than two branches; is saturated; is unsaturated (where an unsaturated alkyl group may have one double bond, two double bonds, more than two double bonds, and/or one triple bond, two triple bonds, or more than three triple bonds); is, or includes, a cyclic structure; is acyclic. Exemplary alkyl groups include $C_1$alkyl (i.e., —$CH_3$ (methyl)), $C_2$alkyl (i.e., —$CH_2CH_3$ (ethyl), —CH═$CH_2$ (ethenyl) and —C≡CH (ethynyl)) and $C_3$alkyl (i.e., —$CH_2CH_2CH_3$ (n-propyl), —CH($CH_3$)$_2$ (I-propyl), —CH═CH—$CH_3$ (1-propenyl), —C≡C—$CH_3$ (1-propynyl), —$CH_2$—CH═$CH_2$ (2-propenyl), —$CH_2$—C≡CH (2-propynyl), —C($CH_3$)═$CH_2$ (1-methylethenyl), —CH($CH_2$)$_2$ (cyclopropyl), and adamantly. The term "alkyl" also includes groups where at least one of the hydrogens of the hydrocarbon group is substituted with at least one of the following: alkyl; "aryl" as defined below; or "hetereoalkyl" as defined below. One or more of the atoms in an alkyl group, with the exception of hydrogen, can be bonded to one or more of the atoms in an adjacent alkyl group, aryl group (aryl as defined below), or heteroalkyl group (heteroalkyl as defined below) to form one or more ring.

The term "aryl" refers to a monocyclic or polycyclic aromatic ring system or a hetereoaromatic ring system containing from 3 to about 30 carbons. The ring system may be monocyclic or fused polycyclic (e.g., bicyclic, tricyclic, etc.). Preferred heteroatoms are nitrogen, oxygen, sulfur, and boron. In various embodiments, the monocyclic aryl ring is C5-C10, or C5-C7, or C5-C6, where these carbon numbers refer to the number of carbon atoms that form the ring system. A C6 ring system, i.e., a phenyl ring, is a preferred aryl group. A C4-S ring system (i.e., a thiophene) is another preferred aryl group. In various embodiments, the polycyclic ring is a bicyclic aryl group, where preferred bicyclic aryl groups are C8-C12, or C9-C10. A naphthyl ring, which has 10 carbon atoms, is a preferred polycyclic aryl group. The term "aryl" also includes groups where at least one of the hydrogens of the aromatic or heteroaromatic ring system is substituted further with at least one of the following: alkyl; halogen; or heteroalkyl (as defined below). One or more of the atoms in an aryl group, with the exception of hydrogen, can be bonded to one or more of the atoms in an adjacent alkyl group, aryl group, or heteroalkyl group (heteroalkyl as defined below) to form one or more rings.

The term "heteroalkyl" refers to an alkyl group (as defined herein) wherein at least one of the carbon atoms or hydrogen atoms is replaced with a heteroatom, with the proviso that at least one carbon atom must remain in the heteroalkyl group after the replacement of carbon or hydrogen with a heteroatom. Preferred heteroatoms are nitrogen, oxygen, sulfur, silicon, and halogen. A heteroatom may, but typically does not, have the same number of valence sites as the carbon or hydrogen atom it replaces. Accordingly, when a carbon is replaced with a heteroatom, the number of hydrogens bonded to the heteroatom may need to be increased or decreased to match the number of valence sites of the heteroatom. For instance, if carbon (valence of four) is replaced with nitrogen (valence of three), then one of the hydrogens formerly attached to the replaced carbon must be deleted. Likewise, if carbon is replaced with halogen (valence of one), then three (i.e., all) of the hydrogens formerly bonded to the replaced carbon must be deleted. Examples of heteroalkyls derived from alkyls by replacement of carbon or hydrogen with heteroatoms is shown immediately below. Exemplary heteroalkyl groups are methoxy (—OCH$_3$), amines (—CH$_2$NH$_2$), nitriles (—CN), carboxylic acids (—CO$_2$H), other functional groups, and dendrons. The term "heteroalkyl" also includes groups where at least one of the hydrogens of carbon or a heteroatom of the heteroalkyl may be substituted with at least one of the following: alkyl; aryl; and heteroalkyl. One or more of the atoms in a heteroalkyl group, with the exception of hydrogen, can be bonded to one or more of the atoms in an adjacent alkyl group, aryl group, or heteroalkyl group to form one or more rings.

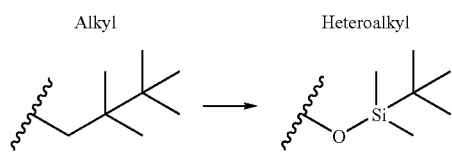

Alkyl     Heteroalkyl

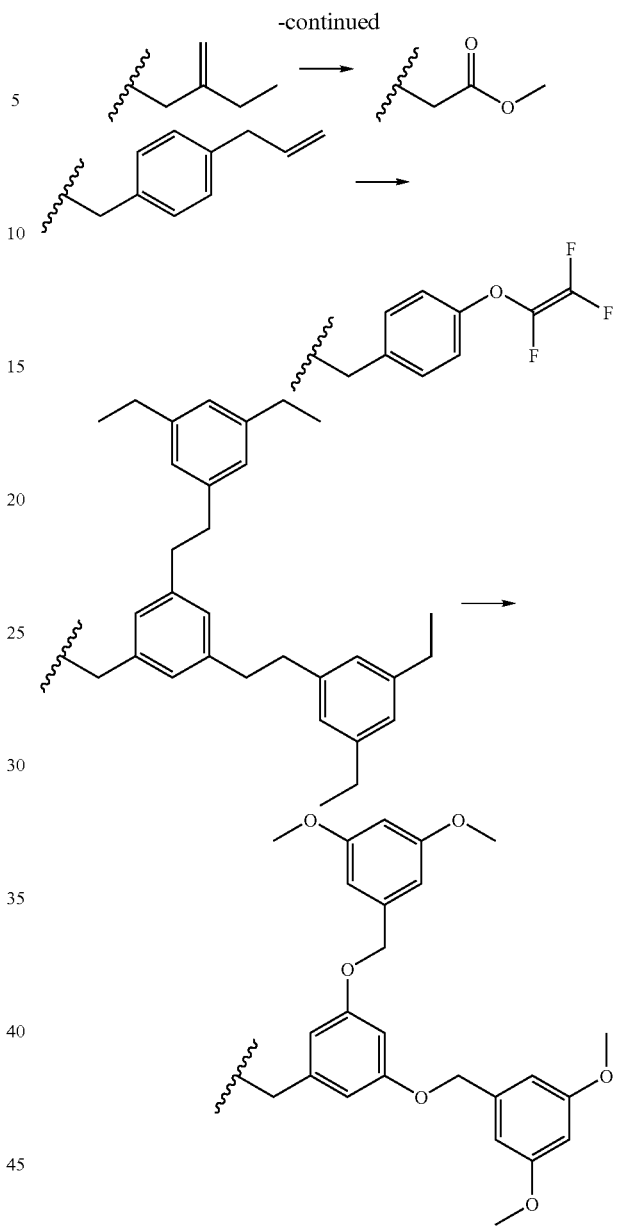

The substituent list that follows is not meant to limit the scope of the definitions above or the inventions described below, but rather merely contains examples of substituents within the definitions above: (1) (alkyl)-CH$_3$, -i-Pr, -n-Bu, -t-Bu, -i-Bu, —CH$_2$CH=CH$_2$ (allyl) -CH$_2$C$_6$H$_5$ (benzyl); (2) (heteroalkyl)-X$_{(0-1)}$(CH$_2$)$_{(0-12)}$(CF$_2$)$_{(0-12)}$(CH$_2$)$_{(0-12)}$CH$_p$Z$_q$ (where X includes —O, —S, —CO$_2$— (ester), Z=halogen, p=0-3, q=0-3, and p+q=3) and branched isomers thereof, —X$_{(0-1)}$(CH$_2$)$_{(0-2)}$(CF$_2$)$_{(0-12)}$(CH$_2$)$_{(0-12)}$Z (where X includes —O, —S, —CO$_2$— (ester), Z includes —OH, —NH$_2$, —CO$_2$H and esters and amides thereof, —COCl, and —NCO) and branched isomers thereof, —OCFCF$_2$ (TFVE), —Si(CH$_3$)$_3$ (TMS), —Si(CH$_3$)$_2$(t-Bu) (TBDMS), —Si(C$_6$H$_5$) (TPS), —Si(C$_6$F$_5$)$_3$, and dendrons such as illustrated in the dendrimers discussed in Bosman, et al., *Chem. Rev.* 99:1665-1688, 1957; (3) (aryl)-C$_6$H$_5$ (phenyl), p-, o-, and/or m-substituted phenyl (with substituents independently selected from —CH$_3$, -i-Pr, -n-Bu, -t-Bu, -i-Bu, —X$_{(0-1)}$(CH$_2$)$_{(0-12)}$(CF$_2$)$_{(0-12)}$(CH$_2$)$_{(0-12)}$CH$_p$Z$_q$ (where X includes —O, —S, —CO$_2$— (ester), Z=halogen, p=0-3, q=0-3, and p+q=3) and branched isomers thereof, —X$_{(0-1)}$(CH$_2$)$_{(0-12)}$(CF$_2$)$_{(0-12)}$(CH$_2$)$_{(0-12)}$Z (where X includes —O, —S, —CO$_2$— (ester), Z includes —OH, —NH$_2$, —CO$_2$H and esters and amides thereof, —TFVE, —COCl, and —NCO) and branched isomers thereof, —Si(CH$_3$)$_3$ (TMS), —Si(CH$_3$)$_2$(t-Bu) (TBDMS), —CH$_2$CH═CH$_2$ (allyl), and TFVE) and dendrons as illustrated in the dendrimers discussed in Bosman, et al., *Chem. Rev.* 99:1665, 1999 or U.S. Pat. No. 5,041,516.

Representative substituents include R$_2$ methyl; trifluoromethyl (see FIG. 1); (CH$_2$)$_n$OCH$_2$OCH$_3$, (CH$_2$)$_n$OCOCH$_3$, and (CH$_2$)$_n$OSi(CH$_3$)$_2$C(CH$_3$)$_3$, where n=3-8; perfluoropyridinyl, perfluorophenyl; and perfluorotoluenyl. Other suitable R$_2$ substituents include halogenated phenyl substituents, such as 3,4-dichlorophenyl, 2,4-dichlorophenyl, and 2,4-difluorophenyl; and alkyl-substituted phenyl substituents, such as 4-cyclohexyl-4'-phenyl and 4-n-butylphenyl; as described in Mingqian, He, et al., "Synthesis of Chromophores with Extremely High Electro-optic Activity. 1. Thiophene-Bridge-Based Chromophores, *Chem. Mater.* 14(11):4662-4668, 2001.

Substituents A$_1$, A$_2$, and A$_3$ can be selected from a variety of functional groups. In one embodiment, substituents A$_1$, A$_2$, and A$_3$ are electron-withdrawing groups to fulfill the electron-withdrawing capability of the acceptor moiety within the nonlinear optically active compound. In one embodiment, substituents A$_2$ and A$_3$ are preferably electron-withdrawing groups. In some embodiments, A$_1$ is an alkyl group. Suitable substituents A$_1$, A$_2$, and A$_3$ include cyano (—CN), nitro (—NO$_2$), ester (—CO$_2$R), trifluoromethylsulfonyl (—SO$_2$CF$_3$), phenylsulfonyl (—SO$_2$Ph), 4-pyridyl, 2-pyridyl, 4-trifluoromethylphenyl, and pentafluorophenyl. Alternatively, A$_2$ and A$_3$ can be taken together to form a cyclic group as described in WO 2004/065384, incorporated herein by reference in its entirety.

In one embodiment, the electron acceptor compounds of the invention are dicyanomethylenedihydrofuran compounds (I.e., A$_2$ and A$_3$ are cyano), as shown in formula (II).

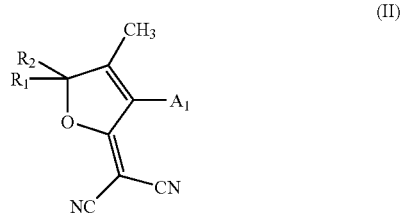

(II)

In one embodiment, A$_1$, A$_2$, and A$_3$ are cyano, as shown in formula (III).

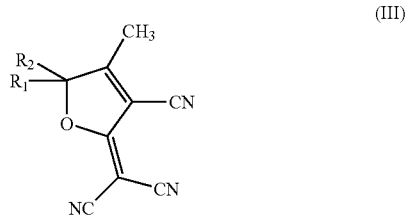

(III)

In one embodiment, A$_1$, A$_2$, and A$_3$ are cyano, R$_2$ is trifluoromethyl, and R$_1$ is an electron rich substituent, as shown in formula (IV).

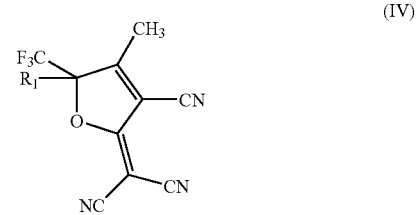

(IV)

The electron acceptor compounds of the invention can be prepared by reacting an appropriately substituted imine compound with an appropriately substituted methylene compound using microwave irradiation as described in WO 2004/065384, incorporated herein by reference in its entirety.

The preparation of representative electron acceptor compounds of the invention is described in Examples 1 and 3-6.

The chemical structures of several representative electron acceptor compounds of the invention (formula IV) are shown in FIG. 1. FIG. 1 illustrates CF$_3$-TCF-type electron acceptors having tunable electron richness and reactive functionalities. Representative electron acceptor compounds of the invention have R$_1$ that is 4-methoxymethyl phenyl ether, 3-methyoxymethyl phenyl ether, 2-thiophenyl, 5-phenyl-2-thiophenyl, and 5-(3-methoxymethyl propyl ether)-2-thiophenyl, respectively.

In another aspect, the present invention provides NLO chromophores that are useful in electro-optic devices. The NLO chromophores include an electron acceptor group derived from the electron acceptor compounds of the invention.

As used herein, the term "chromophore" refers to a compound or moiety that can absorb a photon of light. In the context of the chromophores of the invention, the term "nonlinear" refers second order effects that arise from the nature of the polarizable chromophore (i.e., "push-pull" chromophore moieties) having the general structure D-π-A, where D is an electron donor group, A is an electron acceptor group, and π is a π-bridge group that conjugates the donor group to the acceptor group.

A "donor" (represented by "D") is an atom or group of atoms with low electron affinity relative to an acceptor (defined below) such that, when the donor is conjugated to an acceptor through a π-bridge, electron density is transferred from the donor to the acceptor.

An "acceptor" (represented by "A") is an atom or group of atoms with high electron affinity relative to a donor such that, when the acceptor is conjugated to a donor through a π-bridge, electron density is transferred from the acceptor to the donor. The term "acceptor" refers to the "electron acceptor group" noted above.

A "π-bridge" or "conjugated bridge" (represented in chemical structures by "π" or "π$'$" where n is an integer) is comprised of an atom or group of atoms through which electrons can be delocalized from an electron donor (defined above) to an electron acceptor (defined above) through the orbitals of atoms in the bridge. Preferably, the orbitals will be p-orbitals on multiply bonded carbon atoms such as those found in alkenes, alkynes, neutral or charged aromatic rings, and neutral or charged heteroaromatic ring systems. Additionally, the orbitals can be p-orbitals on multiply bonded atoms such as boron or nitrogen or organometallic orbitals.

The atoms of the bridge that contain the orbitals through which the electrons are delocalized are referred to here as the "critical atoms." The number of critical atoms in a bridge can be a number from 1 to about 30. The critical atoms can also be substituted further with the alkyl, aryl, or heteroalkyl groups, as defined herein. One or more atoms, with the exception of hydrogen, on alkyl, aryl, or heteroalkyl substituents of critical atoms in the bridge may be bonded to atoms in other alkyl, aryl, or heteroalkyl substituents to form one or more rings.

The NLO chromophores of the invention (i.e., D-π-A) are made by reacting an electron acceptor compound of the invention (e.g., compounds having formulas I-IV above) with a donor-bridge compound having an aldehyde functionality (e.g., D-π-CHO) that is reactive toward coupling with the acceptor compound. The reaction of an electron acceptor compound of the invention with a donor-bridge compound having suitably reactive aldehyde functionality to provide an NLO chromophore is illustrated in FIGS. 7-9, 13, and 14.

In another embodiment, the present invention provides a method for making a compound, (i.e., an NLO chromophore) comprising reacting an electron acceptor compound of the invention with a donor-bridge compound having an aldehyde functionality to provide the compound.

In one embodiment, the NLO chromophores of the invention are prepared by reacting an appropriately substituted acceptor compound with appropriately substituted donor-bridge compound using focused microwave irradiation, as described in WO 2004/065384, incorporated herein by reference in its entirety.

Representative chromophores of the invention are illustrated in FIGS. 4, 7, 9, 13, and 14 and their preparations are described in Examples 1, 3, 7, and 8.

The chromophores of the invention are characterized as having high electro-optic coefficients; large hyperpolarizability; large dipole moments; chemical, thermal, electrochemical, and photochemical stability; low absorption at operating wavelengths (e.g., 1.3 and 1.55 μm); suitable solubility in spin casting solvents; compatibility with polymer hosts; and low volatility.

Optical Hyperpolarizability (μβ). Nonlinear optical effects of organic materials depend mainly on the compound's hyperpolarizability (β). A measure of organic chromophore nonlinearity is μβ, where μ is the chromophore dipole moment. A chromophore's optical nonlinearity (μβ) can be measured as described in Dalton et al., "Importance of Intermolecular Interactions in the Nonlinear Optical Properties of Poled Polymers", *Applied Physics Letters*, Vol. 76, No. 11, pp. 1368-1370 (2000).

The chromophores of the invention are characterized as having high optical nonlinearities. In certain embodiments, the invention provides chromophores having optical nonlinearities with μβ greater than about $10,000 \times 10^{-48}$ esu. In other embodiments, chromophores are provided having optical nonlinearities with μβ up to at least about $5,000 \times 10^{-69}$ Cm$^5$/V measured at 1907 nm.

Electro-Optic Coefficient ($r_{33}$). A chromophore's electro-optic coefficient ($r_{33}$) can be measured in a polymer matrix using attenuated total reflection (ATR) technique at telecommunication wavelengths of 1.3 or 1.55 μm. A representative method for measuring the electro-optic coefficient is described in Dalton et al., "Importance of Intermolecular Interactions in the Nonlinear Optical Properties of Poled Polymers", *Applied Physics Letters*, Vol. 76, No. 11, pp. 1368-1370 (2000).

The chromophores of the invention are characterized as having an electro-optic coefficient ($r_{31}$) of at least about 50 pm/V measured at 1.3 or 1.55 μm in polymethylmethacrylate with a compound loading of about 25% by weight based on the total weight of polymethylmethacrylate.

The poling and electro-optic properties of the two chromophores (AJL6 and AJL7) are described below. The preparation of chromophores AJL7 and AJL6 are described in Examples 1 and 2, respectively.

Poling and E-O Properties of AJL7/APC. For the E-O property study, an amorphous polycarbonate (APC, Aldrich poly[Bisphenol A carbonate-co-4,4'-(3,3,5 trimethylcyclohexylidene)diphenol carbonate]) was used as polymer host. The guest host system AJL6-APC and AJL7-APC have a chromophore content of 22~25 wt. % and a solid content of 12 wt. % in cyclopentanone. The samples were spin coated upon the O$_2$ plasma treated ITO glass. The films were soft baked on a hot plate in air for ten minutes at 65° C. then hard baked overnight at 85° C. under vacuum. The resulting film thickness was 1.66 and 1.6 micron, respectively. The films showed excellent optical quality and the UV/VIS were measured.

Figure 2:
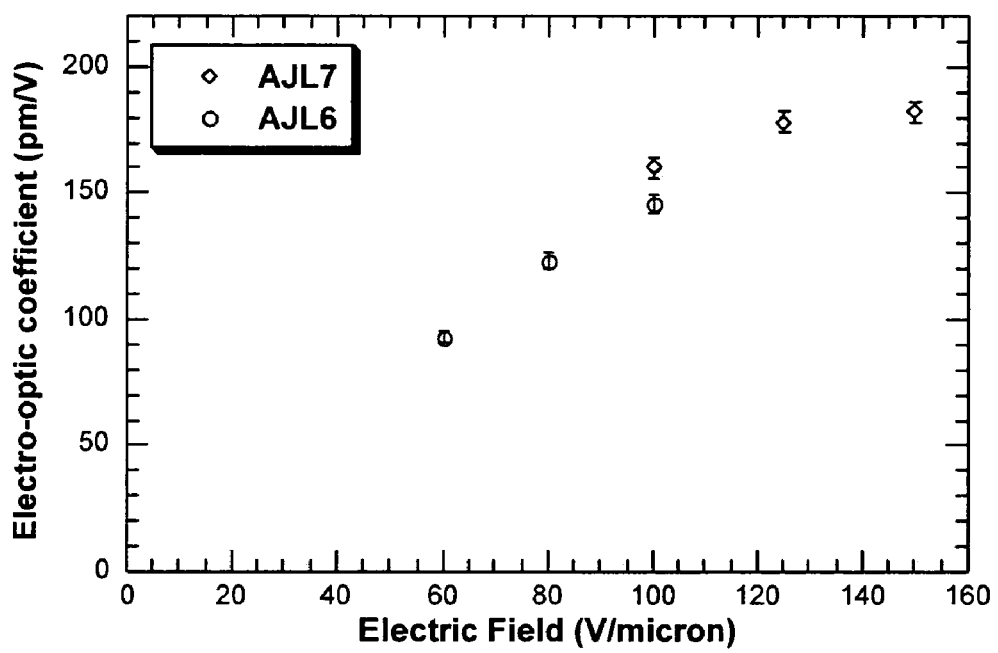
FIG. 2 is a graph comparing the electro-optic coefficient versus electric field for two nonlinear optical chromophore-containing composites.
Figure 3:
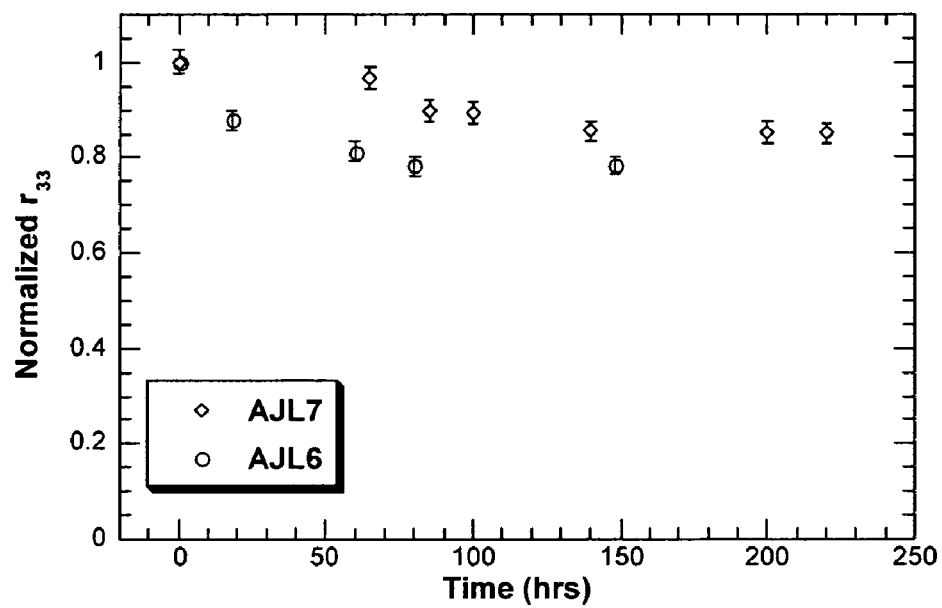
FIG. 3 is a graph comparing the $r_{33}$ value versus time for two nonlinear optical chromophore-containing composites.

FIG. 2 summarizes the contact-poling results for AJL6-APC and AJL7 APC. The E-O coefficient for AJL7/APC was measured to be up to 182 pm/V at 1.3 μm, which is about six times than that of lithium niobate crystal. This may be due to that the rational shape modification and electronic tuning of the acceptor on AJL7 chromophore can greatly improve the poling efficiency of such a high βμ chromophore.

AJL6/APC and AJL7/APC also exhibited temporal stability, retaining about 80% of their original $r_{33}$ value at elevated temperature of 85° C. (FIG. 2). In AJL7/APC, the bulky substituent attached to the acceptor of chromophore prevents the reorientation of the chromophore resulting in the improvement of the thermal stability.

Figure 4:
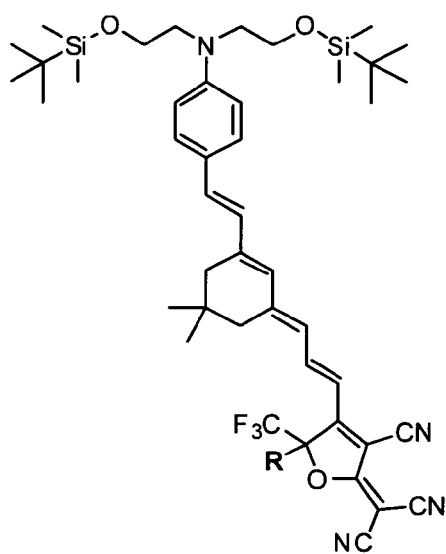
FIG. 4 is an illustration comparing $r_{33}$ value at 1310 nm for three nonlinear optical chromophore-containing composites.

FIG. 4 compares NLO chromophores having different electron acceptor groups (different R$_1$). Referring to FIG. 4, the electro-optic coefficients ($r_{33}$) reported are from the poled films of these chromophores in amorphous polycarbonate (APC, Aldrich): poling voltage is 1.0 MV/cm, and $r_{33}$ values were measured by simple reflection technique at the wavelength of 1310 nm. Chromophore AJL6 (R$_1$=methyl) has a $r_{33}$ value at 1310 nm of 73 pm/V; Chromophore AJL7 (R$_1$=4-methoxymethyl phenyl ether) has a $r_{33}$ value at 1310 mm of 76 pm/V; and Chromophore AJC139 (R$_1$=2-thiophenyl) has a $r_{33}$ value at 1310 nm of 107 pm/V;

Properly tuning the electron-richness of the R$_1$ substituents can maintain and/or improve electron-withdrawing ability of CF$_3$-TCF acceptors, and stabilize the acceptor group. Compared to the pristine CF$_3$-TCF acceptor (R$_1$=CH$_3$, AJL6), the three-dimensional shape of these acceptor groups can avoid the close anti-parallel packing of resultant NLO chromophores and elevate the poling efficiency in suitable matrices. After poling, this three-dimensional bulkiness also can prohibit the free rotation of aligned chromophoric lattice and provide much better temporal stability of eletro-optic activities of their poled polymers.

The functional groups of these electron acceptor compounds of the invention allow for the build up of novel macromolecular architectures having with high EO performance. Through the acceptor compounds of the invention, multi-functionalization provides novel acceptor structures in many different EO polymer systems, such as multi-arm NLO dendrimers, side-chain dendronized NLO polymers, crosslinkable EO polymers, and design optimal molecular and macromolecular engineering with multi-site linkage, thereby achieving the combined advantages of high poling efficiency, excellent thermal, chemical, and photochemical stabilities.

Figure 5:
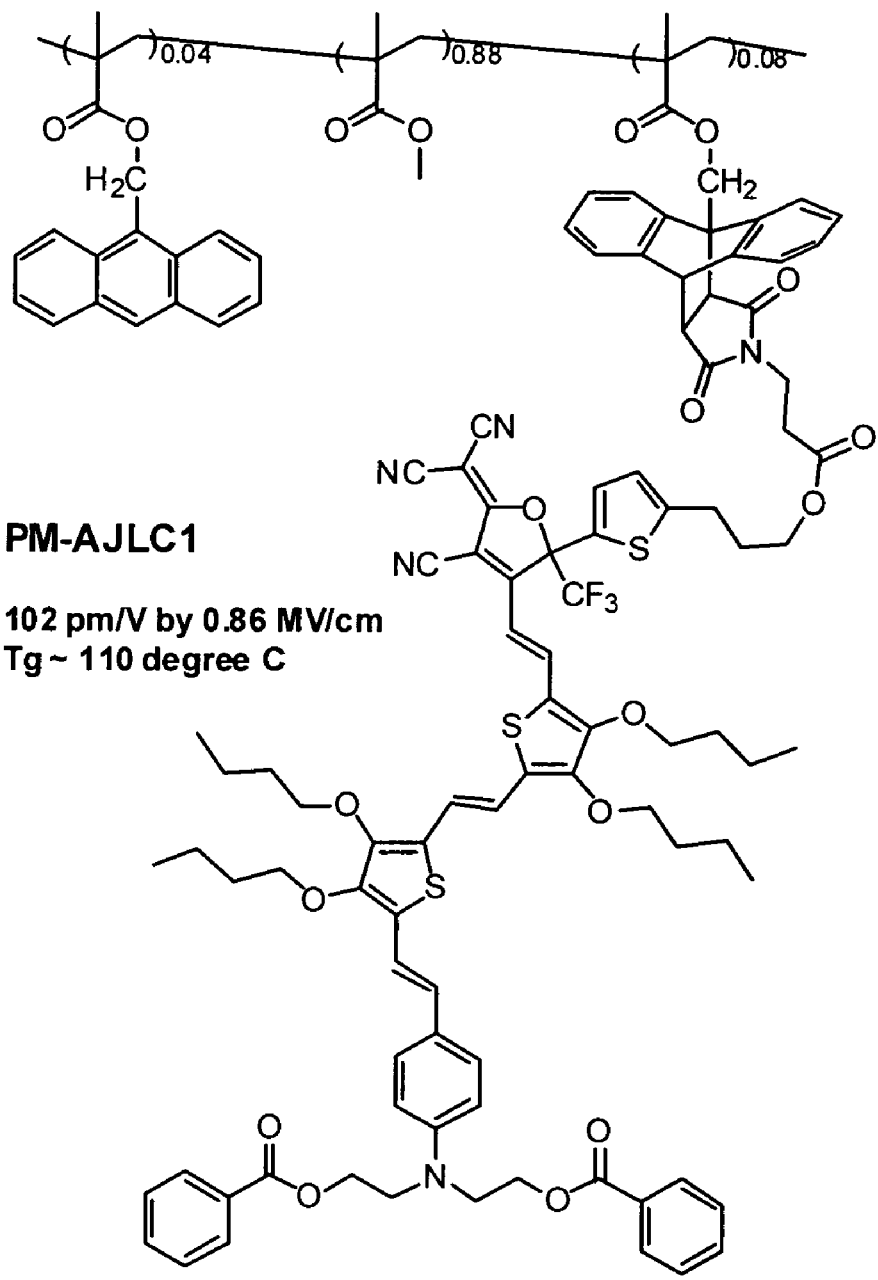
FIG. 5 is an illustration of a representative macromolecular structure of the invention.

A representative macromolecular structure of the invention is illustrated in FIG. 5. FIG. 5 illustrates a double-end functionalized side-chain NLO polymers bearing CF$_3$-TCF-based chromophores. The polymer illustrated in FIG. 5 is a terpolymer having a pendant NLO chromophore substituent grafted to the polymer backbone through the chromophore's acceptor group. The chromophore's acceptor group is derived from an acceptor compound of the invention (see FIG. 1, Compound 6).

Figure 6:
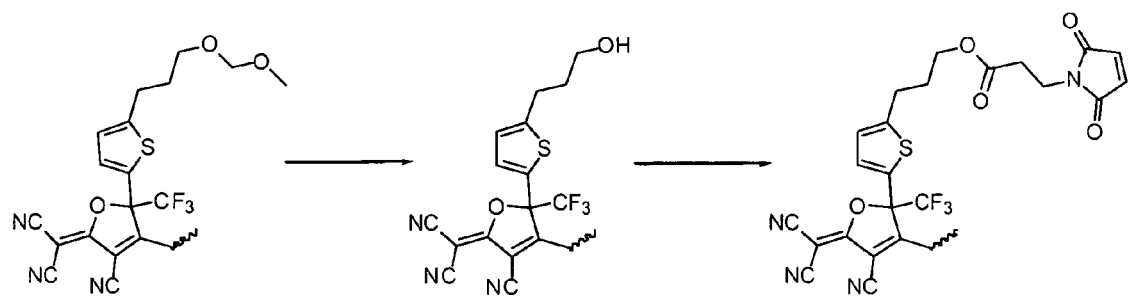
FIG. 6 is a schematic illustration of a method for functionalizing an electron acceptor group useful in preparing a macromolecular structure of the invention.
Figure 7:
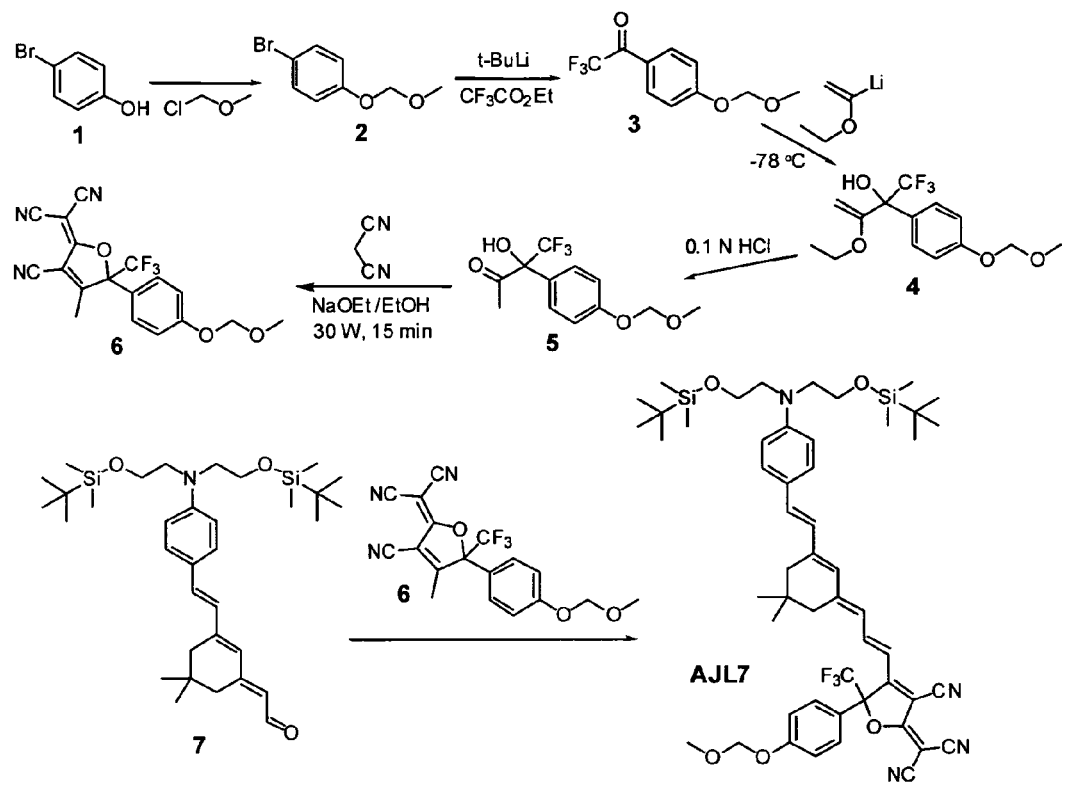
FIG. 7 is a schematic illustration of a method for making a representative nonlinear optical chromophore of the invention.
Figure 8:
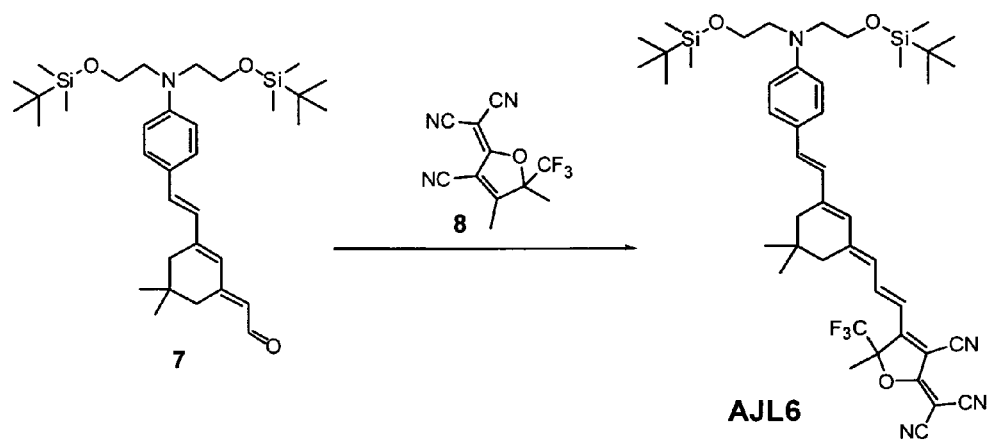
FIG. 8 is a schematic illustration of a method for making a nonlinear optical chromophore.
Figure 9:
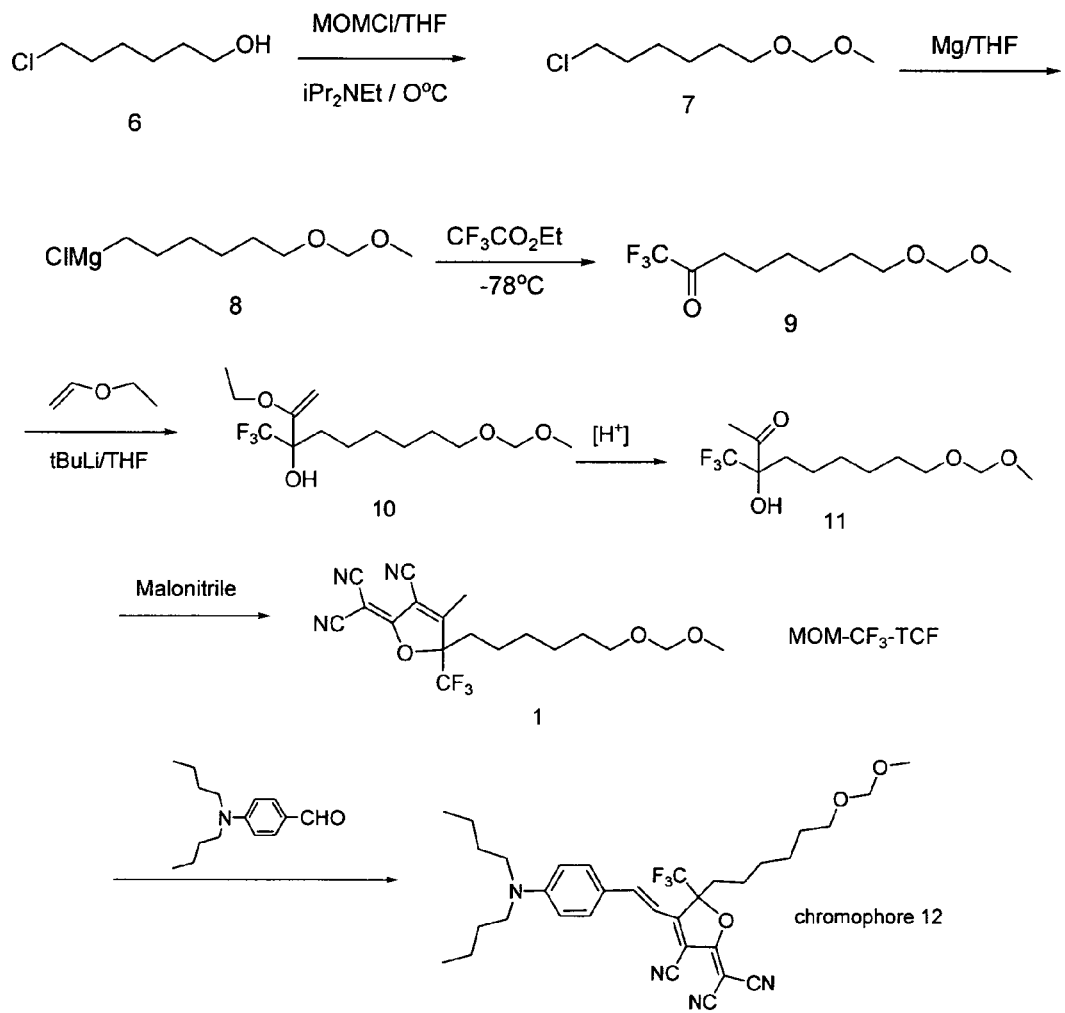
FIG. 9 is a schematic illustration of a method for making a representative electron acceptor compound and a representative nonlinear optical chromophore of the invention.

A representative synthetic route for making a representative functionalized acceptor compound or chromophore (i.e., a maleimide functionalized acceptor compound or chromophore) is illustrated in FIG. 6. The maleimide prepared as shown in FIG. 6 was used to graft to a suitably reactive polymer to provide the macrostructure illustrated in FIG. 5.

In other aspects of the invention, materials (e.g., lattices) that include the nonlinear optical chromophores and devices that include the nonlinear optical chromophores are provided.

The materials and methods described herein can be useful in a variety of electro-optic applications. In addition, these materials and methods may be applied to polymer transistors or other active or passive electronic devices, as well as OLED (organic light emitting diode) or LCD (liquid crystal display) applications.

The use of organic polymers in integrated optics and optical communication systems containing optical fibers and routers has been previously described. The compounds, molecular components, polymers, and compositions (hereinafter, "materials") may be used in place of currently used materials, such as lithium niobate, in most type of integrated optics devices, optical computing applications, and optical communication systems. For instance, the materials may be fabricated into switches, modulators, waveguides, or other electro-optical devices.

For example, in optical communication systems devices fabricated from the chromophores of the invention may be incorporated into routers for optical communication systems or waveguides for optical communication systems or for optical switching or computing applications. Because the materials are generally less demanding than currently used materials, devices made from such chromophores may be more highly integrated, as described in U.S. Pat. No. 6,049,641, which is incorporated herein by reference. Additionally, such materials may be used in periodically poled applications as well as certain displays, as described in U.S. Pat. No. 5,911,018, which is incorporated herein by reference.

Techniques to prepare components of optical communication systems from optically transmissive materials have been previously described, and may be utilized to prepare such components from materials provided by the present invention. Many articles and patents describe suitable techniques, and reference other articles and patents that describe suitable techniques, where the following articles and patents are exemplary:

Eldada, L. and L. Shacklette, "Advances in Polymer Integrated Optics," *IEEE Journal of Selected Topics in Quantum Electronics* 6(1):54-68, January/February 2000; Wooten, E. L., et al. "A Review of Lithium Niobate Modulators for Fiber-Optic Communication Systems," *IEEE Journal of Selected Topics in Quantum Electronics* 6 (1):69-82, January/February 2000; Heismann, F., et al. "Lithium Niobate Integrated Optics Selected Contemporary Devices and System Applications," *Optical Fiber Telecommunications III B*, Academic, Kaminow and Koch (eds.), New York, 1997, pp. 377-462; Murphy, E., "Photonic Switching," *Optical Fiber Telecommunications III B*, Academic, Kaminow and Koch (eds.), New York, 1997, pp. 463-501; E. Murphy, *Integrated Optical Circuits and Components: Design and Applications*, Marcel Dekker, New York, August 1999; Dalton, L., et al., "Polymeric Electro-Optic Modulators: From Chromophore Design to Integration with Semiconductor Very Large Scale Integration Electronics and Silica Fiber Optics," *Ind. Eng. Chem. Res.* 38:8-33, 1999; Dalton, L., et al., "From Molecules to Opto-Chips: Organic Electro-Optic Materials," *J. Mater. Chem.* 9:1905-1920, 1999; Liakatas, I. et al., "Importance of Intermolecular Interactions in the Nonlinear Optical Properties of Poled Polymers," *Applied Physics Letters* 76(11): 1368-1370, Mar. 13, 2000; Cai. C., et al., "Donor-Acceptor-Substituted Phenylethenyl Bithiophenes Highly Efficient and Stable Nonlinear Optical Chromophores," *Organic Letters* 1(11):1847-1849, 1999; Razna, J., et al., "NLO Properties of Polymeric Langmuir-Blodgett Films of Sulfonamide-Substituted Azobenzenes," *J. of Materials Chemistry* 9:1693-1698, 1999; Van den Broeck, K., et al., "Synthesis and Nonlinear Optical Properties of High Glass Transition Polyimides," *Macromol. Chem. Phys* 200:2629-2635, 1999; Jiang, H., and A. K. Kakkar, "Functionalized Siloxane-Linked Polymers for Second-Order Nonlinear Optics," *Macromolecules* 31:2508, 1998; Jen, A. K.-Y., "High-Performance Polyquinolines with Pendent High-Temperature Chromophores for Second-Order Nonlinear Optics," *Chem. Mater.* 10:471-473, 1998; "Nonlinear Optics of Organic Molecules and Polymers," Hari Singh Nalwa and Seizo Miyata (eds.), CRC Press, 1997; Cheng Zhang, Ph.D. Dissertation, University of Southern California, 1999; Galina Todorova, Ph.D. Dissertation, University of Southern California, 2000; U.S. Pat. Nos. 5,272,218; 5,276,745; 5,286,872; 5,288,816; 5,290,485; 5,290,630; 5,290,824; 5,291,574; 5,298,588; 5,310,918; 5,312,565; 5,322,986; 5,326,661; 5,334,333; 5,338,481; 5,352,566; 5,354,511; 5,359,072; 5,360,582; 5,371,173; 5,371,817; 5,374,734; 5,381,507; 5,383,050; 5,384,378; 5,384,883; 5,387,629; 5,395,556; 5,397,508; 5,397,642; 5,399,664; 5,403,936; 5,405,926; 5,406,406; 5,408,009; 5,410,630; 5,414,791; 5,418,871; 5,420,172; 5,443,895; 5,434,699; 5,442,089; 5,443,758; 5,445,854; 5,447,662; 5,460,907; 5,465,310; 5,466,397; 5,467,421; 5,483,005; 5,484,550; 5,484,821; 5,500,156; 5,501,821; 5,507,974; 5,514,799; 5,514,807; 5,517,350; 5,520,968; 5,521,277; 5,526,450; 5,532,320; 5,534,201; 5,534,613; 5,535,048; 5,536,866; 5,547,705; 5,547,763; 5,557,699; 5,561,733; 5,578,251; 5,588,083; 5,594,075; 5,604,038; 5,604,292; 5,605,726; 5,612,387; 5,622,654; 5,633,337; 5,637,717; 5,649,045; 5,663,308; 5,670,090; 5,670,091; 5,670,603; 5,676,884; 5,679,763; 5,688,906; 5,693,744; 5,707,544; 5,714,304; 5,718,845; 5,726,317; 5,729,641; 5,736,592; 5,738,806; 5,741,442; 5,745,613; 5,746,949; 5,759,447; 5,764,820; 5,770,121; 5,76,374; 5,776,375; 5,777,089; 5,783,306; 5,783,649; 5,800,733; 5,804,101; 5,807,974; 5,811,507; 5,830,988; 5,831,259; 5,834,100; 5,834,575; 5,837,783; 5,844,052; 5,847,032; 5,851,424; 5,851,427; 5,856,384; 5,861,976; 5,862,276; 5,872,882; 5,881,083; 5,882,785; 5,883,259; 5,889,131; 5,892,857; 5,901,259; 5,903,330; 5,908,916; 5,930,017; 5,930,412; 5,935,491; 5,937,115; 5,937,341; 5,940,417; 5,943,154; 5,943,464; 5,948,322; 5,948,915; 5,949,943; 5,953,469; 5,959,159; 5,959,756; 5,962,658; 5,963,683; 5,966,233; 5,970,185; 5,970,186; 5,982,958; 5,982,961; 5,985,084; 5,987,202; 5,993,700; 6,001,958; 6,005,058; 6,005,707; 6,013,748; 6,017,470; 6,020,457; 6,022,671; 6,025,453; 6,026,205; 6,033,773; 6,033,774; 6,037,105; 6,041,157; 6,045,888; 6,047,095; 6,048,928; 6,051,722; 6,061,481; 6,061,487; 6,067,186; 6,072,920; 6,081,632; 6,081,634; 6,081,794; 6,086,794; 6,090,322; and 6,091,879.

The foregoing references provide instruction and guidance to fabricate waveguides from materials generally of the types described herein using approaches such as direct photolithography, reactive ion etching, excimer laser ablation, molding, conventional mask photolithography, ablative laser writing, or embossing (e.g., soft embossing). The foregoing references also disclose electron donors and electron bridges that may be incorporated into the chromophores of the invention or that may also incorporate an electron donor and/or electron bridges described herein.

Components of optical communication systems that may be fabricated, in whole or part, with materials according to the present invention include, without limitation, straight waveguides, bends, single-mode splitters, couplers (including directional couplers, MMI couplers, star couplers), routers, filters (including wavelength filters), switches, modulators (optical and electro-optical, e.g., birefringent modulator, the Mach-Zender interferometer, and directional and evanescent coupler), arrays (including long, high-density waveguide arrays), optical interconnects, optochips, single-mode DWDM components, and gratings. The materials described herein may be used with, for example, wafer-level processing, as applied in, for example, vertical cavity surface emitting laser (VCSEL) and CMOS technologies.

In many applications, the materials described herein may be used in lieu of lithium niobate, gallium arsenide, and other inorganic materials that currently find use as light-transmissive materials in optical communication systems.

The materials described herein may be used in telecommunication, data communication, signal processing, information processing, and radar system devices and thus may be used in communication methods relying, at least in part, on the optical transmission of information. Thus, a method according to the present invention may include communicating by transmitting information with light, where the light is transmitted at least in part through a material including a chromophore of the invention or related macrostructure.

The materials of the present invention can be incorporated into various electro-optical devices. Accordingly, in another aspect, the invention provides electro-optic devices including the following:

an electro-optical device comprising a chromophore or related macrostructure according to the present invention;

a waveguide comprising a chromophore or related macrostructure according to the present invention;

an optical switch comprising a chromophore or related macrostructure according to the present invention;

an optical modulator comprising a chromophore or related macrostructure according to the present invention;

an optical coupler comprising a chromophore or related macrostructure according to the present invention;

an optical router comprising a chromophore or related macrostructure according to the present invention;

a communications system comprising a chromophore or related macrostructure according to the present invention;

a method of data transmission comprising transmitting light through or via a chromophore or related macrostructure according to the present invention;

a method of telecommunication comprising transmitting light through or via a chromophore or related macrostructure according to the present invention;

a method of transmitting light comprising directing light through or via a chromophore or related macrostructure according to the present invention;

a method of routing light through an optical system comprising transmitting light through or via a chromophore or related macrostructure according to the present invention;

an interferometric optical modulator or switch, comprising: (1) an input waveguide; (2) an output waveguide; (3) a first leg having a first end and a second end, the first leg being coupled to the input waveguide at the first end and to the output waveguide at the second end; and (4) and a second leg having a first end and a second end, the second leg being coupled to the input waveguide at the first end and to the output waveguide at the second end, wherein at least one of the first and second legs includes a chromophore or related macrostructure according to the present invention;

an optical modulator or switch, comprising: (1) an input; (2) an output; (3) a first waveguide extending between the input and output; and (4) a second waveguide aligned to the first waveguide and positioned for evanescent coupling to the first waveguide; wherein at least one of the first and second legs includes a chromophore or related macrostructure according to the present invention, the modulator or switch may further including an electrode positioned to produce an electric field across the first or second waveguide; and an optical router comprising a plurality of switches, wherein each switch includes: (1) an input; (2) an output; (3) a first waveguide extending between the input and output; and (4) a second waveguide aligned to the first waveguide and positioned for evanescent coupling to the first waveguide; wherein at least one of the first and second legs includes a chromophore or related macrostructure according to the present invention, the plurality of switches may optionally be arranged in an array of rows and columns.

To summarize, two novel highly efficient NLO chromophores AJL6 and AJL7 have been synthesized. In poled guest-host polymers doped with AJL7 chromophore, exceptionally large and thermally stable electro-optic coefficients (up to 182 pm/V at 1.3 μm) has been achieved, indicating the proper shape and electronic modification on the electron-withdrawing group of chromophore AJL7 can greatly improve the alignment efficiency and stability. This material and its derivatives can be considered as very promising candidates for high-speed electro-optic modulators with very low $V_\pi$.

The following examples are provided for the purpose of illustrating, not limiting, the present invention.

EXAMPLES

Example 1

The Preparation of a Representative Electron Acceptor Compound and Representative NLO Chromophore Made From the Acceptor: AJL7

In this example, the preparation of a representative chromophore of the invention, AJL7, is described. In the following preparations, yields are based on $^1$H NMR of clean separated compounds after purification by column chromatography. The preparation is described in reference to FIG. 7.

Preparation of compound 2. To a stirred solution of 17.3 g (100 mmol) of 1 and 10.47 g (130 mmol) of chloromethyl methyl ether in 120 ml of methylene chloride was added 14.2 g (110 mmol) of diisopropylethyl amine slowly with stirring at 0° C. The resulting solution was stirred for one hour and the mixture was left to warm up to room temperature overnight with stirring. The reaction solution was washed with 5% NaHCO$_3$ aqueous solution, dried, and the solvent was removed via rotary evaporation. Compound 2 was purified via a flash chromatography over silica gel with 5% ethyl acetate in hexane to give a yellow oil (15 g, 67%). $^1$H NMR (CDCl$_3$): δ 7.36 (d, 2H, 9.3 Hz), 6.90 (d, 2H, 9.3 Hz), 5.12 (s, 2H), 3.45 (s, 3H).

Preparation of compound 3. To a solution of 6.51 g (30 mmol) of 2 in 100 ml of diethyl ether was added 35.3 ml (60 mmol) of solution of t-BuLi in pentane (1.7M) at −78° C. over 30 min and the mixture was stirred for additional 3 hours at −78° C. under nitrogen. The temperature of the reaction mixture was raised to 0° C. until the formation of white solid (lithiated 2) and recooled to −78° C. before the addition of 5.68 g (40 mmol) of ethyl trifluoroacetate in 30 ml of diethylether slowly over the period of 30 min, and the mixture was stirred for 3 hours at −78° C. The reaction was poured into 100 ml of sat. $NH_4Cl$ aqueous solution and the mixture was extracted with diethyl ether (100 ml×2). The combined organic layer was washed with water and dried over anhydrous magnesium sulfate and the solvent was evaporated. The residue was chromatographed over silica gel using 8% ethyl acetate in hexane to give 3 as a yellow oil (6.3 g, 90%). $^1$H NMR ($CDCl_3$): δ 8.04 (d, 2H, 8.8 Hz), 7.12 (d, 2H, 8.8 Hz), 5.25 (s, 2H), 3.47 (s, 3H).

Preparation of compound 4. To a solution of 3.25 g (45 mmol) of ethyl vinyl ether in 40 ml of THF was added 17.7 ml (30 mmol) of t-BuLi in pentane (1.7M) dropwise at −78° C. under nitrogen. The solution was warmed on an ice bath and stirred for one hour and then re-cooled to −78° C. A solution of 3.53 g (15 mmol) of 3 in 5 ml of THF was added the lithiated enol ether solution dropwise at −78° C. The resulting mixture was stirred for one hour at −78° C. and allowed to warm up to room temperature slowly for 2 hours. The reaction was then quenched with 30 ml of sat. $NH_4Cl$ aqueous solution. The organic layer was separated and the aqueous layer was extracted with diethyl ether (50 ml×2). The combined organic layer was washed with water and dried over magnesium sulfate and the solvent was evaporated to give crude 4 as yellow oil (4.4 g, 96%). The crude product was used in the subsequent reaction without further purification.

Preparation of compound 5. To a solution of 3 g (10 mmol) of crude 4 in 10 ml of methanol was added 0.1 ml of 1 N HCl solution dropwise at room temperature. The reaction was monitored by TLC using 20% ethyl acetate in hexane (Rf ~0.5). After stirring for 2 hours, the resulting mixture was neutralized with 5% $NaHCO_3$ and the solvent was evaporated via rotary evaporator and extracted with diethyl ether (50 ml×2). The combined organic layer was washed with 50 ml of water and dried over magnesium sulfate and the solvent was evaporated. The residue oil was chromatographed over silica gel using 20% ethyl acetate in hexane to give yellow oil (1.63 g, 59%). $^1$H NMR ($CDCl_3$): δ 7.47 (d, 2H, 8.8 Hz), 7.06 (d, 2H, 8.8 Hz), 5.17 (s, 2H), 4.88 (s, 1H), 3.46 (s, 3H), 2.30 (s, 3H).

Preparation of compound 6. To a mixture of 1.63 g (5.84 mmol) of 5 and 849 mg (12.8 mmol) of malononitrile in 5 ml of ethanol was added 1 ml of 1 M solution of sodium ethoxide in ethanol. The mixture was irradiated under focused 30 W microwave for 15 min. The resulting mixture was concentrated and purified through chromatography on silica gel with a gradient eluent of methyl chloride to 1% methanol in methylene chloride to afford 6 as a greenish oil (1 g, 46%). $^1$H NMR ($CDCl_3$): δ 7.31 (d, 2H, 8.3 Hz), 7.15 (d, 2H, 8.3 Hz), 5.20 (s, 2H), 4.46 (s, 3H), 2.44 (s, 3H).

Preparation of chromophore AJL7. To 5 mL of dry ethanol was added 0.45 g (0.77 mmol) of 7 and 0.29 g (0.77 mmol) of 6. The mixture was heated to 70° C. under nitrogen atmosphere for 30 mins and monitored by TLC. The crude product was purified through chromatography on silica gel with the eluent of 5-10% ethyl acetate in hexane to afford AJL7 as crystalline powder (0.28 g, 40%), which was been recrystallized in methanol twice prior to use.

Example 2

The Preparation of NLO Chromophore: AJL6

In this example, the preparation of an NLO chromophore, AJL6, is described. In the following preparations, yields are based on $^1$H NMR of clean separated compounds after purification by column chromatography. The preparation is described in reference to FIG. 8.

Preparation of chromophore AJL6. To 5 mL of dry ethanol was added 0.292 g (0.50 mmol) of 7 and 0.133 g (0.52 mmol) of 8, prepared as described in Example 1. The mixture was heated to 70° C. under nitrogen atmosphere for 1 hr. The crude precipitated product was been recrystallized in methanol twice prior to use (0.27 g, 66%).

Example 3

The Preparation of a Representative Electron Acceptor Compound and a Representative NLO Chromophore Made Using the Acceptor Compound In this example, the preparation of a representative acceptor compound of the invention and a representative NLO chromophore made from the acceptor compound is described. The preparation is described with reference to FIG. 9.

Compound 7: $iPr_2NEt$ (31 ml) was dropped into alcohol 8 (19.8 g) and MOMCl (12.6 g) in THF (110 ml) cooled in ice bath. The reaction was left overnight at room temperature. Hexane (150 ml) was added to push the precipitation of salt from solution. The salt was filtered. The filtrate was washed with brine, dried over $Na_2SO_4$, evaporated and distilled to give a liquid (24.3 g). $^1$H-NMR ($CDCl_3$, TMS): δ 4.62 (s, 2H, $OCH_2O$), 3.54 (tt, 4H, $OCH_2$ and $CH_2Cl$), 3.37 (s, 3H, $OCH_3$), 1.80 (m, 2H, $CH_2$), 1.62 (m, 2H, $CH_2$), 1.45 (m, 4H, $CH_2CH_2$).

Compound 9: Compound 7 (12.1 g) was added to Mg (1.44 g) in THF with one small iodine crystal at 60-65° C. After addition, the reaction was refluxed for 45 min to give a Compound 3 in solution. This solution was transferred to $CF_3CO_2Et$ in THF at −78° C. The resulted reaction solution was stirred at room temperature for 20 min before wet workup. The product was distilled to give a liquid (Compound 9, 10.6 g). $^1$H-NMR ($CDCl_3$, TMS): δ 4.63 (s, 2H, $OCH_2O$), 3.54 (tt, 2H, $OCH_2$), 3.39 (s, 3H, $OCH_3$), 2.73 (t, 2H, $COCH_2$), 1.73 (m, 2H, $CH_2$), 1.64 (m, 2H, $CH_2$), 1.43 (m, 4H, $CH_2CH_2$).

Compound 11: t-BuLi (1.7 M, 29 ml) was dropped into vinyl ethyl ether (3.75 g) in THF (25 ml) at −78° C. during 15 min. After 30 min, the temperature was brought to −15° C. in 40 min before recooling to −78° C. and adding Compound 9 (6.0 g). The reaction was kept overnight before quenching with brine and 0.5N HCl. The product was extracted with ether. After drying over $Na_2SO_4$ and evaporation, the product (Compound 10) was used without further purification, $^1$H-NMR showed good purity. The product was dissolved in methanol (10 ml) and 1N HCl (10 ml) at room temperature for 1.2 hours. The reaction was neutralized with aqueous $NaHCO_3$ and the product extracted with methylene chloride. Column chromatography (hexanes/ethyl acetate=4:1-1:1) gave a liquid (Compound 11, 2.87 g). $^1$H-NMR ($CDCl_3$, TMS): δ 4.63 (s, 2H, $OCH_2O$), 4.35 (s, 1H, OH), 3.54 (t, 2H, $OCH_2$), 3.38 (s, 3H, $OCH_3$), 2.38 (s, 3H, $CH_3$), 1.99 (t, 2H, $CH_2$), 1.59 (m, 4H, $CH_2$), 1.39 (m, 6H, $CH_2CH_2$).

Acceptor 1: Compound 11 (572 mg), malononitrile (284 mg), and NaOEt in ethanol (1M, 0.2 ml) and 0.5 ml of ethanol was heated under 20-35 W microwave. The product purified by chromatography was viscous liquid at room temperature that solidified in a freezer. $^1$H-NMR ($CDCl_3$, TMS): δ 4.63 (s, 2H, OCH$_2$O), 3.53 (t, 2H, OCH$_2$), 3.38 (s, 3H, OCH$_3$), 2.39 (t, 3H, C≡CCH$_3$), 1.99 (t, 2H, CH$_2$), 1.59 (m, 4H, CH$_2$), 1.39 (m, 6H, CH$_2$CH$_2$).

Chromophore 12: Dibutylaminobenzaldehyde (50 mg) was mixed with Acceptor 1 (50 mg) in ethanol. The reaction was stirred at room temperature overnight. The chromophore was purified by column chromatography to give a green crystal. $^1$H-NMR (CDCl$_3$, TMS): δ 8.09 (d, 1H, CH=), 7.59 (d, 2H, Ar), 6.71 (d, 2H, Ar), 6.64 (d, 1H, CH=), 4.61 (s, 2H, OCH$_2$O), 3.53 (t, 2H, OCH$_2$), 3.44 (t, 4H, CH$_2$), 3.36 (s, 3H, OCH$_3$), 2.1-2.4 (m, 2H, CH$_2$), 1.65 (m, 8H, CH$_2$), 1.38 (m, 10H, CH$_2$), 0.99 (t, 6H, CH$_3$).

Example 4

The Preparation of a Representative Electron Acceptor Compound

Figure 10:
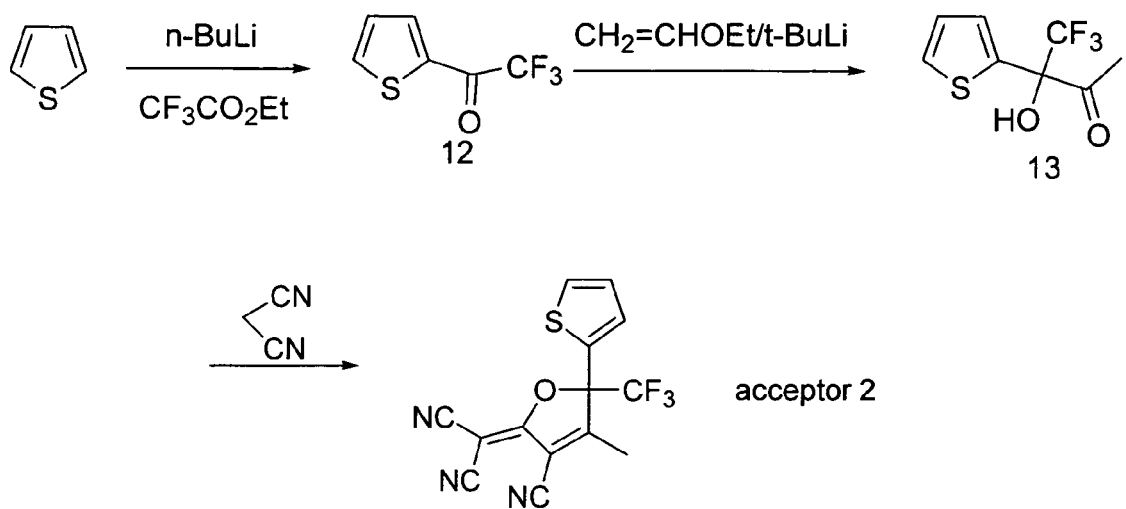
FIG. 10 is a schematic illustration of a method for making a representative electron acceptor compound of the invention.

In this example, the preparation of a representative acceptor compound of the invention is described. The preparation is described with reference to FIG. 10.

Compound 12: BuLi (2.5M, 38 ml) was added to thiophene (8.0 g) in THF (45 ml) at −78° C. After 30 min, this solution was transferred into CF$_3$CO$_2$Et in THF at −78° C. The reaction was brought to 0° C. during 2 hours. The reaction then was quenched by dilute aqueous HCl. The product was purified by distillation to give a clear liquid (Compound 12, 7.9 g). $^1$H-NMR (CDCl$_3$, TMS): δ 7.99 (m, 1H, thiophene), 7.93 (dd, 1H, thiophene) 7.28 (dd, 2H, thiophene).

Compound 13: this compound was synthesized following a similar procedure of synthesis of Compound 11 described in Example 3. $^1$H-NMR (CDCl$_3$, TMS): δ 7.41 (d, 1H, thiopnene), 7.37 (m, 1H, thiophene) 7.10 (dd, 2H, thiophene), 5.22 (s, 2H, OH), 2.49 (s, 3H, CH$_3$).

Acceptor 2: A mixture of Compound 13 (1.121 g), malonitrile (0.72 g), sodium ethoxide in ethanol (1M, 1 ml) in a 25 ml flask with a magnetic stir bar was heated with 15-25 W microwave at 95-105° C. for 40 min. to give Acceptor 2 (0.49 g) after column chromatography. $^1$H-NMR (CDCl$_3$, TMS): δ 7.64 (dd, 1H, thiophene), 7.38 (d, 1H, thiophene), 6.71 (dd, 1H, thiophene), 2.55 (s, 3H, CH$_3$).

Example 5

The Preparation of a Representative Electron Acceptor Compound

Figure 11:
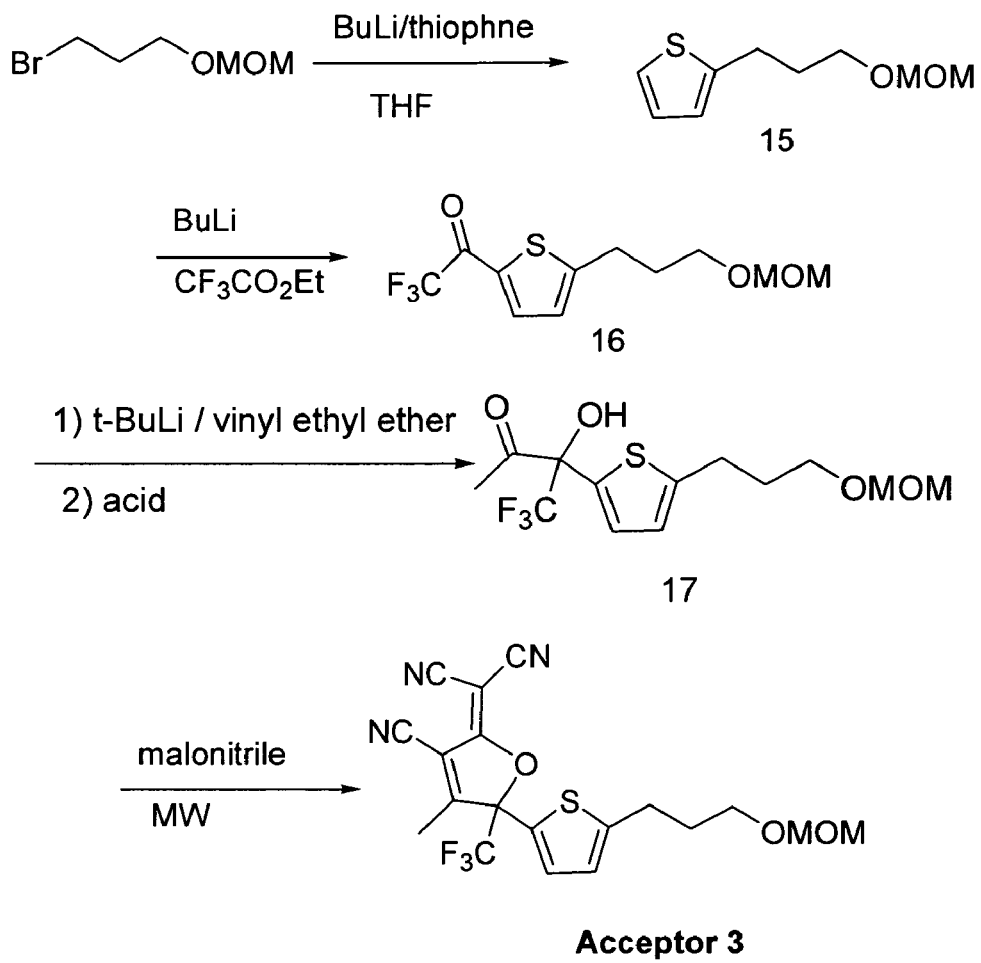
FIG. 11 is a schematic illustration of a method for making a representative electron acceptor compound of the invention.

In this example, the preparation of a representative acceptor compound of the invention is described. The preparation is described with reference to FIG. 11.

Compound 15: BuLi (1.79M, 19 ml) was added to thiophene in THF at −78° C. After stirring for 30 min, Br(CH$_2$)$_3$OMOM was added slowly to the mixture. The reaction was kept stirring overnight and then was heated to reflux for 3 hours. The reaction was quenched with brine and organic layer was separated and dried over Na$_2$SO$_4$. After removal of solvent, the product was distilled to give a clear liquid (4.60 g). $^1$H-NMR (CDCl$_3$, TMS): δ 7.12 (d, 1H, thiopnene), 6.91 (dd, 1H, thiophene) 6.80 (d, 2H, thiophene), 4.63 (s, 2H, OCH$_2$O), 3.57 (t, 2H, OCH$_2$), 3.37 (s, 3H, CH$_3$), 2.93 (t, 2H, CH$_2$), 1.97 (tt, 2H, CH$_2$).

Compound 16: BuLi (1.6M, 15.6 ml) was added to compound 15 in THF (50 ml) at −78° C. After stirring for 45 min, CF$_3$CO$_2$Et (3.62 g) was added slowly to the mixture. The reaction was kept stirring overnight. The reaction was quenched with brine and organic layer was separated and dried over Na$_2$SO$_4$. After removal of solvent, the product was distilled to give a clear liquid (6.52 g). $^1$H-NMR (CDCl$_3$, TMS): δ 7.84 (d, 1H, thiopnene), 6.99 (d, 1H, thiophene), 4.65 (s, 2H, OCH$_2$O), 3.60 (t, 2H, OCH$_2$), 3.39 (s, 3H, CH$_3$), 3.05 (t, 2H, CH$_2$), 2.02 (tt, 2H, CH$_2$).

Compound 17: t-BuLi (1.6M, 26.7 ml) was dropped into vinyl ethyl ether (4.326 g) in THF (50 ml) at −78° C. After 30 min the temperature was brought to −15° C. in 70 min before recooling to −78° C. and adding compound 16 (6.0 g). The reaction was kept overnight before quenching with brine and 0.5N HCl. Extraction of product with ether was applied. After drying over Na$_2$SO$_4$ and evaporation, the product was used without further purification. The product was dissolved in methanol (30 ml) and 1N HCl (15 ml) at room temperature for 2 hours. The reaction was neutralized with aqueous NaHCO$_3$ and extracted with methylene chloride. Column chromatography (hexanes/ethyl acetate=4:1-1:1) to give a liquid (7.12 g). $^1$H-NMR (CDCl$_3$, TMS): δ 7.18 (d, 1H, thiopnene), 6.79 (d, 1H, thiophene), 4.64 (s, 2H, OCH$_2$O), 3.60 (t, 2H, OCH$_2$), 3.38 (s, 3H, CH$_3$), 2.94 (t, 2H, CH$_2$), 2.48 (s, 3H, CH$_3$), 1.98 (tt, 2H, CH$_2$).

Acceptor 3: Compound 17 (0.652 g, 2 mmol) was mixed with malonitrile (0.330 g, 5 mmol) in a 25 ml flask equipped with a condenser. To this mixture, 0.3 ml of ethanol was added under nitrogen. The mixture was stirred until a clear solution was formed. Then, LiOEt (1.0M, 0.2 ml) was injected using a syringe. The flask was irradiated under 10-40 W microwave for 20 to 60 min. The final reaction mixture was evaporated on rotary evaporator. The residue was purified using column chromatography (methylene chloride/ethyl acetate=10:0.5) to provide Acceptor 3 (80-100 mg). Changing the microwave irradiation time from 20 to 60 min, temperature/microwave power, catalyst (e.g., NaOEt, t-BuOK, LiOH, iPr$_2$NEt, NH$_4$Oac), solvent (e.g., butanol, chlorobenzene) and cooling method, the yield did not increase significantly. $^1$H-NMR (CDCl$_3$, TMS): δ 7.09 (d, 1H, thiophene), 6.72 (d, 1H, thiophene), 4.64 (s, 2H, OCH$_2$O), 3.63 (t, 2H, OCH$_2$), 3.39 (s, 3H, CH$_3$), 2.91 (t, 2H, CH$_2$), 2.53 (s, 3H, CH$_3$), 1.98 (tt, 2H, CH$_2$).

Example 6

The Preparation of a Representative Electron Acceptor Compound

Figure 12:
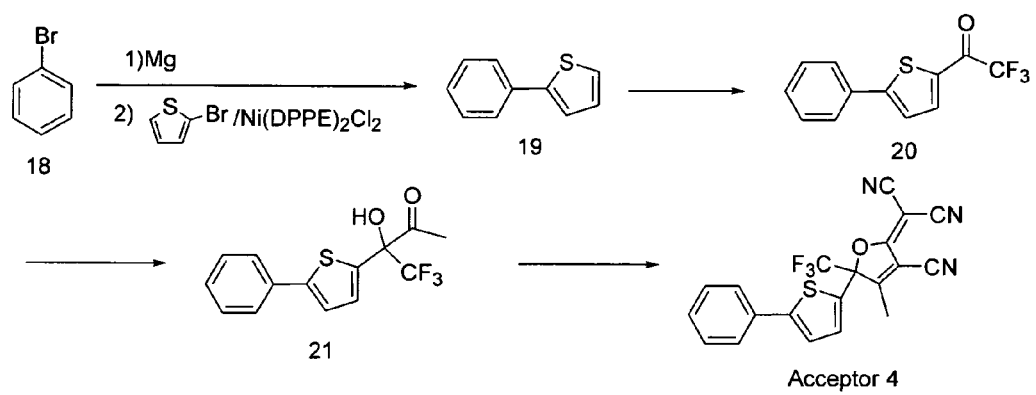
FIG. 12 is a schematic illustration of a method for making a representative electron acceptor compound of the invention.
Figure 13:
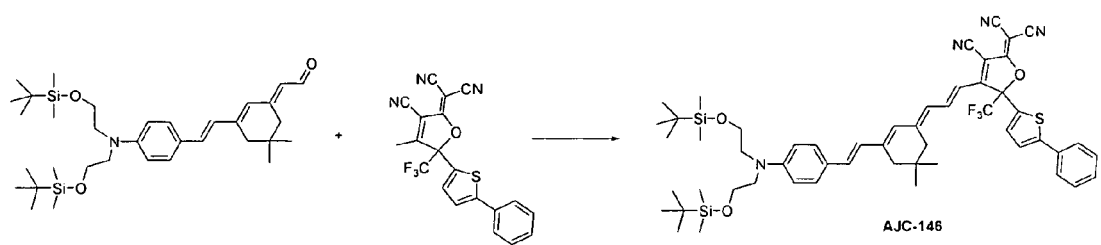
FIG. 13 is a schematic illustration of a method for making a representative nonlinear optical chromophore of the invention.
Figure 14:
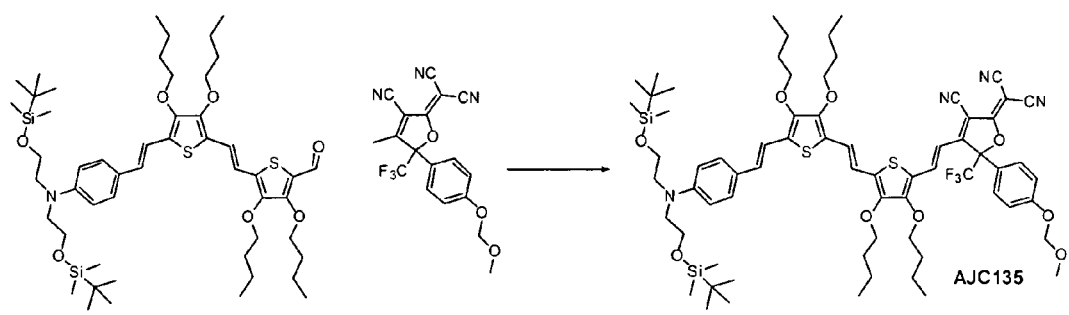
FIG. 14 is a schematic illustration of a method for making a representative nonlinear optical chromophore of the invention.

In this example, the preparation of a representative acceptor compound of the invention is described. The preparation is described with reference to FIG. 12.

Compound 19: In a dry 3-necked flask equipped with an additional funnel, 8.64 g of Mg powder was charged with 500 mg of iodine crystals under nitrogen. Dry THF was injected using syringe transferring technique. Then, 2 mL of bromobenzene in THF (50 mL) was added dropwise into flask. The flask was warmed with heating to reflux to initiate the reaction, once the iodine color is gone, heating was removed. The residual bromobenzene solution was added in such a speed that the reaction was in gentle reflux through whole addition period. After completion of this addition, the flask was heated to reflux for additional 1 hour. The reaction was cooled to about 35° C. Then this solution was transferred via cannula to another flask charge with 2-bromothiophene (47.2 g) in THF (50 ml) cooled in ice bath. During the transfer period, the reaction temperature was controlled below 18° C. by adjusting the adding speed. After this addition, the reaction was heated at 40° C. overnight. The reaction was quenched by adding aqueous ammonium chloride solution (100 ml) and 1N HCl aqueous solution (50 ml). The organic layer was separated, the aqueous layer was extracted with methylene chloride. The combined organic layers were dried over MgSO$_4$, filtered, evaporated, and distilled to give Compound 19 (51.2 g). $^1$H-NMR (CDCl$_3$, TMS): δ 7.61 (d, 2H, phenyl), 7.40 (m, 3H, phenyl), 7.33 (dd, 1H, thiophene), 7.30 (dd, 1H, thiophene), 7.10 (dd, 1H, thiophene).

Compound 20: BuLi (2.5M, 42 ml) was added to Compound 19 in THF (100 ml) at −78° C. After this addition, the temperature was allowed to rise to −40° C. The temperature was lowered to −78° C., then $CF_3CO_2Et$ (3.62 g) was added slowly to the mixture. The reaction was kept stirring overnight. The reaction was quenched with brine and organic layer was separated and dried over $Na_2SO_4$. After removal of solvent, the product was purified by silica gel column to give a yellowish leaf-like crystals (12.3 g). $^1$H-NMR ($CDCl_3$, TMS): δ 8.1 (d, 2H, phenyl), 7.45 (m, 3H, phenyl), 7.43 (dd, 1H, thiophene), 7.39 (dd, 1H, thiophene), 7.38 (dd, 1H, thiophene).

Compound 21: this compound was synthesized following a similar procedure of synthesis of Compound 11 described in Example 3. Yield: 37%. $^1$H-NMR ($CDCl_3$, TMS): δ 7.60 (d, 2H, phenyl), 7.41 (m, 2H, thiophene and phenyl) 7.34 (t, 2H, phenyl), 7.28 (d, 1H, thiophene), 5.25 (s, 1H, OH), 2.54 (s, 3H, $CH_3$).

Acceptor 4: a mixture of Compound 20 (0.60 g), malonitrile (0.33 g), sodium ethoxide in ethanol (1M, 0.1 ml) and ethanol (0.9 ml) in a 25 ml flask with a magnetic stir bar was heated with 15-25 W microwave at 95° C. for 40 min to give Acceptor 4 (119 mg) after column chromatography. $^1$H-NMR ($CDCl_3$, TMS): δ 7.60 (m, 2H, thiophene), 7.43 (m, 3H, thiophene) 7.33 (m, 2H, thiophene), 2.58 (s, 3H, $CH_3$).

Example 7

The Preparation of a Representative NLO Chromophore

In this example, the preparation of a representative NLO chromophore (AJC146) made using electron acceptor compound of the invention is described. The preparation is described with reference to FIG. 13.

To 0.5 mL of dry ethanol was added 0.161 g (0.270 mmol) of the bridge aldehyde and 0.108 g (0.272 mmol) of the acceptor compound prepared as described in Example 6. The mixture was heated to 40° C. under nitrogen atmosphere for two and a half hours. The crude product was purified through chromatography on silica gel eluting with 5-10% ethyl acetate in hexane to afford AJC146 as dark powder (0.191 g, yield: 73%), which was recrystallized in methanol twice prior to use. $^1$H-NMR ($CDCl_3$, TMS): δ 8.27 (d, 1H, CH=), 7.62 (d, 1H, thiophene), 7.41 (d, 3H, phenylene and CH=), 7.29 (m, 1H para-phenylene), 6.96 (d, 1H, CH=), 6.83 (d, 1H, CH=), 6.72 (d, 2H, phenylene), 6.43 (d, 1H, thiophene), 6.38 (d, 1H, CH=), 3.80 (t, 4H, $CH_2O$), 3.59 (t, 4H, $CH_2N$), 2.41 (m, 4H, $CH_2$ of cyclohexylene), 1.03 (m, 6H, $CH_3$ on cyclohexylene), 0.90 (m, 18H, $CH_3$ of t-butyl), 0.04 (s, 12H, $CH_3$ of TBDMS). Glass transition temperature by DSC: $T_g$=65° C.

Example 8

The Preparation of a Representative NLO Chromophore

In this example, the preparation of a representative NLO chromophore (AJC135) made using electron acceptor compound of the invention is described. The preparation is described with reference to FIG. 14.

The aldehyde bridge (0.753 g, 0.8 mmol) and the acceptor compound (0.375 g, 1.0 mmol), prepared as described in Example 1, were dissolved in anhydrous ethanol (1.0 mL) and the mixture was stirred at around 50° C. for 4 hours. The crude product was purified by flash chromatography and recrystallization in methanol/methylene dichloride several times to afford AJC135 as dark solid (yield: 48%). $^1$H-NMR ($CDCl_3$, TMS): δ 7.97 (d, 1H, CH=), 7.45 (d, 2H, Ar), 7.35 (d, 3H, Ar+CH=), 7.28 (d, 1H, CH=), 7.16 (d, 2H, Ar) 7.05 (d, 11H, CH=), 6.89 (d+d, 2H, CH=), 6.73 (d, 2H, Ar), 6.56 (d, 2H, CH=), 5.24 (s, 2H, $OCH_2O$), 4.20 (t+t, 4H, $CH_2O$), 4.07 (t, 2H, $CH_2O$), 4.01 (t, 2H, $CH_2O$), 3.80 (t, 4H, $CH_2O$), 3.57 (t, 4H, $NCH_2$), 3.51 (s, 3H, $CH_3O$), 1.79 (m, 6H, $CH_2$ of butyl), 1.68 (m, 2H, $CH_2$ of butyl), 1.57 (m, 6H, $CH_2$ of butyl), 1.41 (m, 2H, $CH_2$ of butyl), 1.0 (m, 9H, $CH_3$ of butyl), 0.97 (t, 3H, $CH_3$ of butyl), 0.92 (s, 18H, $CH_3$ of t-butyl group on TBDMS), 0.07 (s, 12H, $CH_3$ of TBDMS). Glass transition temperature by DSC: $T_g$=47° C.

While the preferred embodiment of the invention has been illustrated and described, it will be appreciated that various changes can be made therein without departing from the spirit and scope of the invention.

The invention claimed is:

1. A compound having the formula:

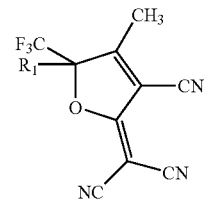

wherein $R_1$ is selected from the group consisting of 4-methoxymethyl phenyl ether, 3-methoxymethyl phenyl ether, 2-thiophenyl, 5-phenyl-2-thiophenyl, and 5-(3-methoxymethyl propyl ether)-2-thiophenyl.

2. A nonlinear optical chromophore, comprising a donor group (D) conjugated to an acceptor group (A) through a π-bridge group (π) having the formula D-π-A, wherein A has the formula:

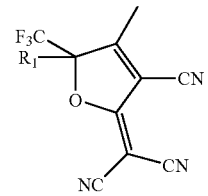

wherein $R_1$ is selected from the group consisting of 4-methoxymethyl phenyl ether, 3-methoxymethyl phenyl ether, 2-thiophenyl, 5-phenyl-2-thiophenyl, and 5-(3-methoxymethyl propyl ether)-2-thiophenyl.

3. A method for making a nonlinear optical chromophore having a donor group (D) conjugated to an acceptor group (A) through a π-bridge group (π) and having the formula D-π-A, comprising reacting a donor-bridge compound having an aldehyde functionality and having the formula D-π-CHO with an acceptor compound having the formula:

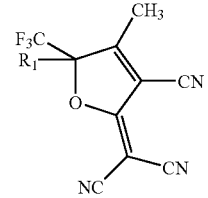

wherein $R_1$ is selected from the group consisting of 4-methoxymethyl phenyl ether, 3-methoxymethyl phenyl ether, 2-thiophenyl, 5-phenyl-2-thiophenyl, and 5-(3-methoxymethyl propyl ether)-2-thiophenyl.

* * * * *